US008568452B2

(12) United States Patent
Voorhies

(10) Patent No.: US 8,568,452 B2
(45) Date of Patent: Oct. 29, 2013

(54) LUMBAR DISC REPLACEMENT IMPLANT FOR POSTERIOR IMPLANTATION WITH DYNAMIC SPINAL STABILIZATION DEVICE AND METHOD

(75) Inventor: Rand M. Voorhies, New Orleans, LA (US)

(73) Assignee: Rand M. Voorhies, New Orleans, LA (US)

( * ) Notice: Subject to any disclaimer, the term of this patent is extended or adjusted under 35 U.S.C. 154(b) by 0 days.

(21) Appl. No.: 13/432,927

(22) Filed: Mar. 28, 2012

(65) Prior Publication Data

US 2012/0203345 A1 Aug. 9, 2012

Related U.S. Application Data

(62) Division of application No. 11/796,059, filed on Apr. 26, 2007, now Pat. No. 8,241,362.

(51) Int. Cl.
*A61B 17/70* (2006.01)

(52) U.S. Cl.
USPC ........... 606/246; 606/253; 606/256; 606/257; 606/259

(58) Field of Classification Search
USPC ................................. 606/246–279
See application file for complete search history.

(56) References Cited

U.S. PATENT DOCUMENTS

| 1,268,932 | A | 6/1918 | Corrigan |
| 2,783,758 | A | 3/1957 | Trott |
| 3,648,691 | A | 3/1972 | Lumb |
| 3,858,578 | A * | 1/1975 | Milo .............................. 600/229 |
| 3,872,861 | A | 3/1975 | Tamny |
| 4,448,191 | A | 5/1984 | Rodnyansky |
| 4,697,582 | A | 10/1987 | William |
| 4,728,329 | A | 3/1988 | Mansat |
| 4,743,260 | A | 5/1988 | Burton |
| 4,917,700 | A | 4/1990 | Aikins |
| 5,011,484 | A | 4/1991 | Bréard |
| 5,027,802 | A | 7/1991 | Donohue |
| 5,074,291 | A | 12/1991 | Carter |
| 5,092,866 | A | 3/1992 | Breard |
| 5,180,393 | A | 1/1993 | Commarmond |
| 5,282,863 | A | 2/1994 | Burton |
| 5,387,213 | A | 2/1995 | Breard |
| 5,415,661 | A | 5/1995 | Holmes |
| 5,451,203 | A | 9/1995 | Lamb |
| 5,540,688 | A | 7/1996 | Navas |
| 5,609,634 | A | 3/1997 | Voydeville |
| 5,649,541 | A | 7/1997 | Stuckey |
| 5,649,925 | A * | 7/1997 | Barbera Alacreu ......... 606/86 A |
| 5,672,175 | A | 9/1997 | Martin |
| 5,961,516 | A | 10/1999 | Graf |
| 5,980,522 | A | 11/1999 | Koros et al. ................ 623/17.11 |
| 5,984,922 | A | 11/1999 | McKay |

(Continued)

Primary Examiner — Jerry Cumberledge
(74) Attorney, Agent, or Firm — Streets & Steele; Patrick K. Steele; Jeffrey L. Streets

(57) ABSTRACT

The invention consists of disc replacement implant for the lumbar spine designed for insertion into the disc space via a posterior approach. The implant can be stabilized in the disc space by connection to the vertebra or can be connected to dynamic spinal stabilization device consisting of interconnected bullets nested in a spring nested in a woven sleeve. By controlling the limits of elongation and compression the device prevents movement beyond normal physiological limits. In the midrange of movement flexibility is allowed. A method for using the dynamic spinal stabilization device is also provided.

14 Claims, 20 Drawing Sheets

(56) References Cited

U.S. PATENT DOCUMENTS

| | | | |
|---|---|---|---|
| 6,176,882 B1 | 1/2001 | Biedermann et al. ...... 623/17.15 |
| 6,293,949 B1 | 9/2001 | Justis | |
| 6,296,643 B1 | 10/2001 | Hopf | |
| 6,296,644 B1 | 10/2001 | Saurat | |
| 6,440,169 B1 | 8/2002 | Elberg | |
| 6,530,934 B1* | 3/2003 | Jacobsen et al. ............. 606/157 |
| 6,723,126 B1 | 4/2004 | Berry .................. 623/17.11 |
| 6,966,910 B2 | 11/2005 | Ritland | |
| 6,986,771 B2 | 1/2006 | Paul | |
| 6,989,011 B2 | 1/2006 | Paul | |
| 7,029,475 B2 | 4/2006 | Panjabi | |
| 7,083,621 B2* | 8/2006 | Shaolian et al. ........... 606/86 A |
| 7,338,525 B2 | 3/2008 | Ferree ....................... 623/17.11 |
| 7,634,874 B2* | 12/2009 | Lucas ............................ 52/108 |
| 7,635,389 B2 | 12/2009 | Yu et al. .................... 623/17.15 |
| 7,713,304 B2 | 5/2010 | Ankney et al. ............. 623/17.16 |
| 7,722,674 B1 | 5/2010 | Grotz ........................ 623/17.11 |
| 7,785,325 B1* | 8/2010 | Milbank ....................... 606/62 |
| 7,785,351 B2 | 8/2010 | Gordon et al. ............. 606/259 |
| 7,799,081 B2 | 9/2010 | McKinley ................. 623/17.16 |
| 7,828,825 B2* | 11/2010 | Bruneau et al. ............. 606/260 |
| 2002/0095154 A1 | 7/2002 | Atkinson | |
| 2002/0107524 A1 | 8/2002 | Magana | |
| 2002/0120270 A1 | 8/2002 | Trieu | |
| 2002/0133155 A1 | 9/2002 | Ferree | |
| 2002/0151978 A1 | 10/2002 | Zacouto | |
| 2003/0056427 A1 | 3/2003 | Graf | |
| 2003/0171749 A1 | 9/2003 | Le Couedic | |
| 2003/0220642 A1 | 11/2003 | Freudiger | |
| 2003/0220643 A1 | 11/2003 | Ferree | |
| 2004/0049189 A1 | 3/2004 | Le Couedic | |
| 2004/0049190 A1 | 3/2004 | Biedermann | |
| 2004/0143264 A1 | 7/2004 | McAfee | |
| 2005/0120269 A1 | 6/2005 | Larson | |
| 2005/0131407 A1* | 6/2005 | Sicvol et al. .................... 606/61 |
| 2005/0177157 A1* | 8/2005 | Jahng .............................. 606/61 |
| 2005/0240266 A1 | 10/2005 | Kuiper | |
| 2005/0277922 A1* | 12/2005 | Trieu et al. ...................... 606/61 |
| 2005/0283247 A1 | 12/2005 | Gordon | |
| 2006/0004447 A1 | 1/2006 | Mastrorio et al. ......... 623/17.11 |
| 2006/0036240 A1* | 2/2006 | Colleran et al. ................. 606/61 |
| 2006/0084991 A1 | 4/2006 | Borgstrom | |
| 2006/0085073 A1 | 4/2006 | Raiszadeh | |
| 2006/0085074 A1 | 4/2006 | Raiszadeh | |
| 2006/0142758 A1 | 6/2006 | Petit | |
| 2007/0093813 A1* | 4/2007 | Callahan et al. ................ 606/61 |
| 2009/0088799 A1* | 4/2009 | Yeh ................................ 606/246 |

* cited by examiner

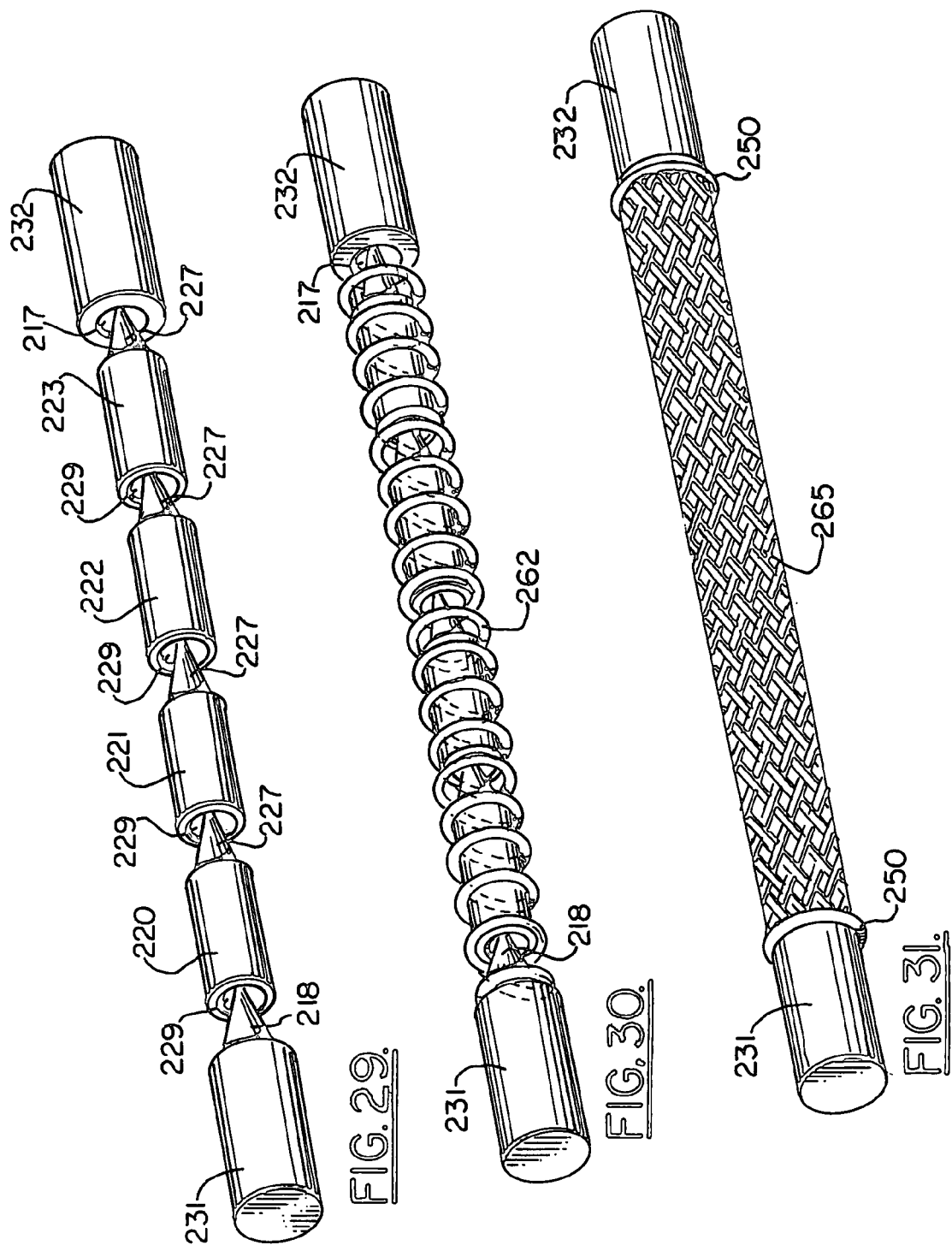

FIG. 38.
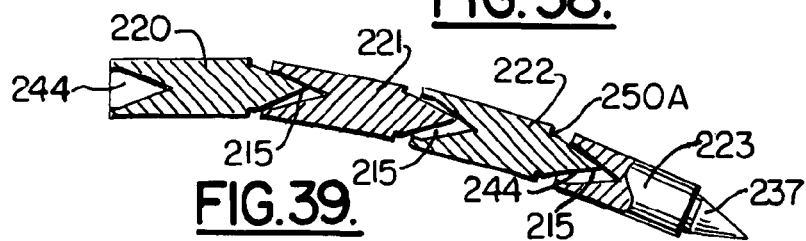
FIG. 39.
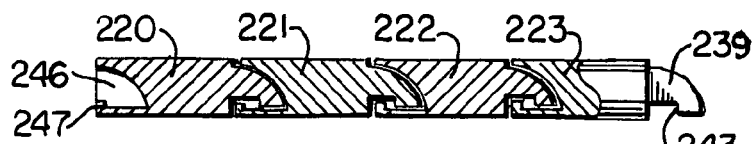
FIG. 40.
FIG. 41.
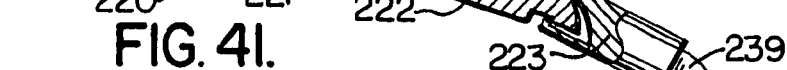
FIG. 42.
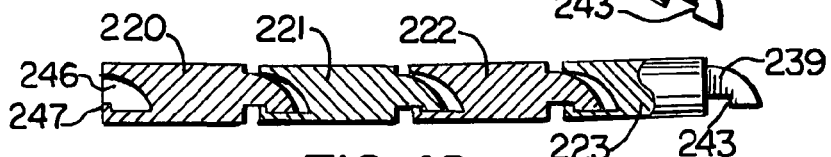
FIG. 43.
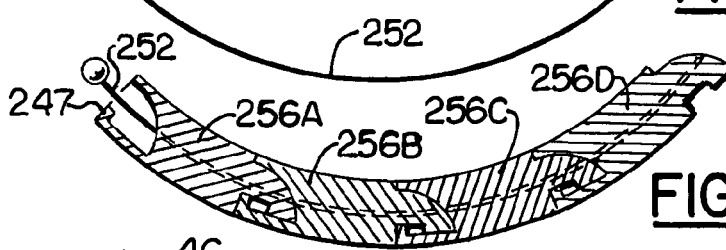
FIG. 44.
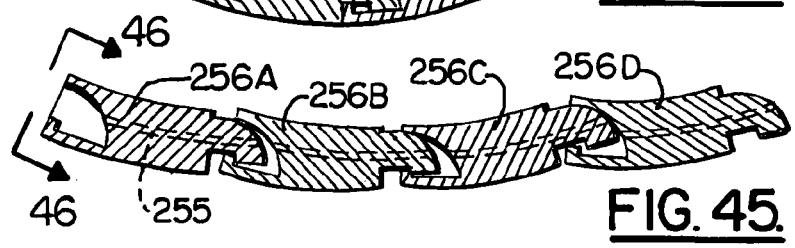
FIG. 45.
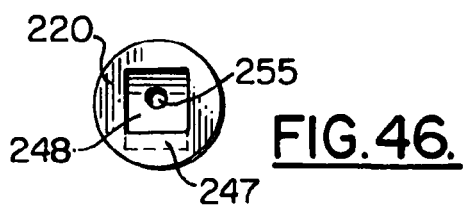
FIG. 46.

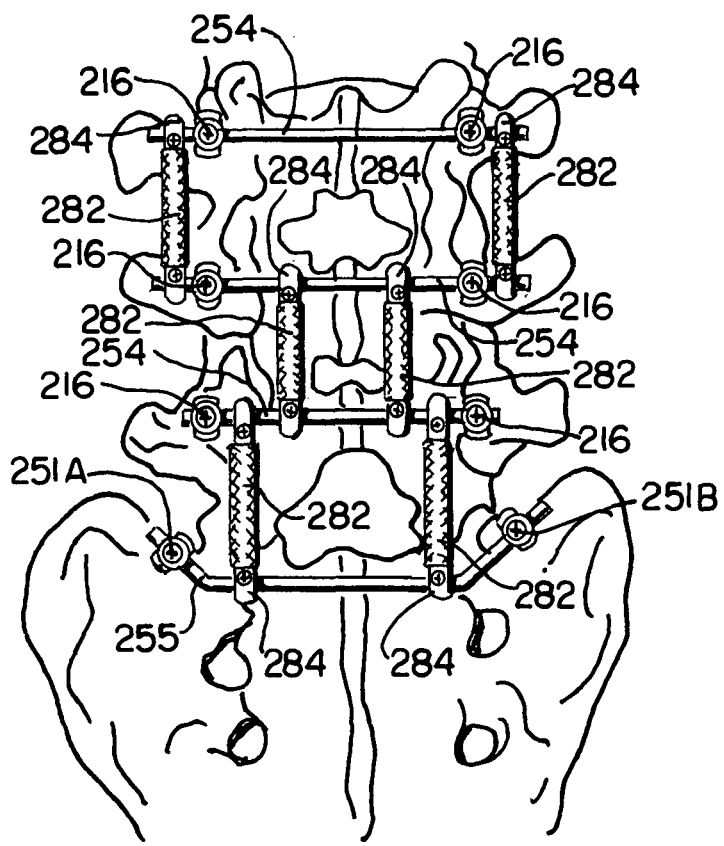
FIG. 49.
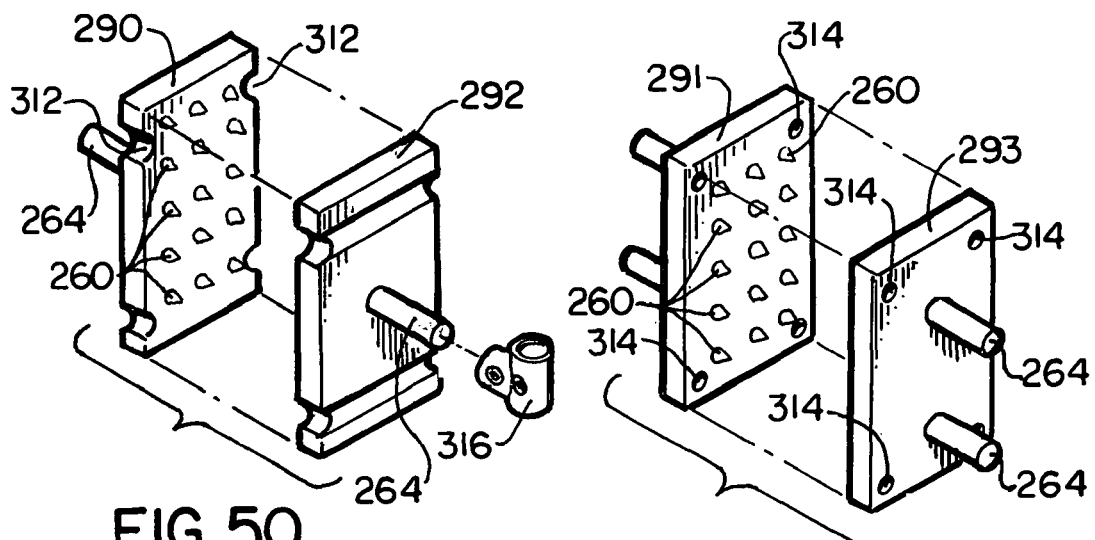
FIG. 50.
FIG. 51.

LUMBAR DISC REPLACEMENT IMPLANT FOR POSTERIOR IMPLANTATION WITH DYNAMIC SPINAL STABILIZATION DEVICE AND METHOD

CROSS-REFERENCE TO RELATED APPLICATION

This application is a divisional of U.S. application Ser. No. 11/796,059 filed Apr. 26, 2007, granted on Aug. 14, 2012 as U.S. Pat. No. 8,241,362, the disclosure of which is incorporated herein by reference for all purposes.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

1. Field of the Invention

The invention relates to a lumbar spine disc replacement apparatus with accompanying stabilization for the spine and method. The present invention is an artificial disc that can be implanted by a posterior surgical approach that can be used with devices and methods for dynamic stabilization of spinal vertebrae in a manner that permits motion within physiological normal range. The device provides mechanical resistance and support when the spine attempts to move beyond the desired limits.

2. Description of the Prior Art

Low back pain is an extremely important and costly public health issue, accounting for a significant proportion of the health care costs of modem industrialized nations. Conservative or non-operative treatment programs are the mainstay of therapy for this condition. This approach includes physical therapy, exercise programs, cognitive behavioral therapy, anti-inflammatory medications either orally or by spinal injection, and by modification in the work place environment and activities of daily living. Sometimes, however, pain and disability persist and surgical intervention becomes an option.

In general, there are two distinct but overlapping clinical problems, which often occur together. The first is termed sciatica, which is caused by compression of a spinal nerve either as the result of disc protrusion or bony compression. The second is axial joint pain, which results from painful degeneration of the joints of the spinal motion segment. A spinal motion segment consists of two vertebrae which are jointed together naturally by three joints: the intervertebral disc in the front of the spine; and the paired symmetrical facet joints in the back of the spine. The surrounding ligaments, tendons and muscle tissues are also important components of the spinal motion segment.

The surgical treatment for sciatica involves the physical unpinching of the compressed spinal nerve by removing the bulging disc or the bony spurs either alone or in combination. By taking the pressure off of the nerve, the irritation is eliminated and the sensation of pain and/or tingling numbness in the leg is relieved. Hopefully too the loss of strength in the affected muscles will also disappear in time. Unpinching a nerve, however, is not expected to have much affect on any low back pain which may be coexisting.

The surgical option for axial joint pain has traditionally involved a lumbar arthrodesis, also known as a fusion. A fusion operation is designed to stop and eliminate all motion in the spinal motion segment by destruction of some or all of the joints of the spinal motion segment. Bone graft material as well as rigid implanted fixating devices are employed for this purpose. By eliminating movement at the symptomatic spinal motion segment the expectation is that the low back pain will be reduced. The disadvantage to this approach is the loss of spinal flexibility. Additionally some authorities believe that a rigid fusion will place increased stress on neighboring spinal motion segments, thereby accelerating the degenerative and aging process. If these adjacent motion segments become symptomatic, then additional surgical intervention could become necessary on these previously non symptomatic areas.

One alternative approach to a rigid spinal fusion is the concept of joint replacement, either partial or total. The strategy is similar to joint replacement surgery in other areas of the body, such as with advanced degenerative changes in the hips or knees. In the spinal area, this involves the removal of some or all of the joints of the spinal motion segment accompanied by replacement with a mechanical device designed to replicate the function of the joint that had been removed.

Many examples of devices designed to replace the intervertebral disc or the facet joints exist. The most common approach to designing artificial spinal discs has contemplated surgical implantation using an anterior approach. This procedure requires an access surgeon skilled in mobilizing the large and dangerous blood vessels that obscure the site for insertion into the front of the disc. By nature of the anatomy, it is difficult or impossible to see and correct any pinched nerves when operating in this approach. Furthermore, extremely accurate placement of the artificial disc is essential to allow for the proper functioning of the implant. Damage to internal organs in the abdominal cavity, and damage to small nerves on the front of the spinal column resulting in retrograde ejaculation are additional concerns. Perhaps the greatest drawback to the anterior approach is the question of dealing with implant failure or displacement.

Revision surgery in this setting is recognized as extremely dangerous and even life threatening due to the scar tissue that has developed around the blood vessels located in front of the spine. Mobilizing these blood vessels the first time when the artificial disc is being initially inserted is challenging, especially because of the wide exposure needed to be certain that the disc is correctly positioned. Mobilizing these same blood vessels for repeat surgery carries a very high risk of serious complication or even death. Interference with the circulation to the lower limbs can have devastating consequences. Massive blood loss from tears in the veins stuck down by scar tissue can be fatal. Even if only a small number of anteriorly placed artificial discs require removal, the percentage of complications is anticipated to be unacceptably high.

For this reason, a posterior approach for implantation of an artificial disc for the lumbar spine would be preferred by many spine surgeons. By its nature, this approach permits and even mandates complete visualization of the nerves, so that any compressed neural structures can be unpinched. Furthermore, the potential abdominal complications, including damage to internal organs, possible retrograde ejaculation, and the risk to the major blood vessels supplying circulation to the lower limbs are avoided.

The main risk of the posterior approach is to the neural elements themselves. These include the nerve roots that are exiting the spinal canal as well as the central grouping of nerve roots called the cauda equina. The risk to these structures occurs during placement and surgical implantation of the device. Should the implant become dislodged, move, or migrate, then those structures are again at risk.

The first risk, occurring at the time of surgical implantation, can be minimized in two ways. The first is by the design of the implant, and the second is proper surgical technique. This requires adequate exposure of the posterior side regions of the disc, so that the implant can be inserted without any damage to the neural elements.

In order to achieve this goal, it is necessary to remove enough of the bony structures covering the lateral regions of the disc. This results in the surgical destruction of the facet joints, so that generally facet joint replacement devices are utilized in conjunction with artificial discs implanted using a posterior approach. The second major risk of this type of implant is the risk of subsequent dislodgment or migration, which could also damage the neural elements. This hazard is avoided by insuring that the posteriorly placed artificial disc is firmly attached and anchored to the vertebral bone.

There are a multitude of patents and patent application Publications pertaining to artificial disc prostheses designed for implantation via an anterior or transabdominal approach. However implants intended for posterior insertion in the disc space are not as common. Devices intended not to replace the entire disc, but only the internal cushion portion called the nucleus pulposus are less technically challenging. Examples of inventions intended to accomplish this limited objective are disclosed in U.S. Pat. Pub. Nos. 2006/0064172 and 2006/0100304. Shape memory material is inserted through a relatively small opening in the posterior aspect of the outer thick layer of the disc called the annulus fibrosus. The material then expands or uncoils filling the cavity in the center of the disc where the nucleus pulposus formerly resided. The material is intended to recreate the cushion or shock absorber characteristics of the nucleus. The strong outer ligamentous layer of the disc, the annulus fibrosus, continues to provide strength and stability. Furthermore, the facet joints are left undisturbed.

There are several other devices that are designed for partial rather than total disc replacement. By partial disc replacement, only the inner component called the nucleus pulposus is replaced. However, there are several drawbacks to the strategy of partial disc replacement. There is a high risk for displacement or extrusion, since there is no firm anchoring strategy for the implants. For one thing, the degenerative processes that result in the need for surgical intervention rarely affect the nucleus pulposus in isolation. Indeed the other components of the spinal motion segment joint complex are often similarly affected. Therefore treatment aimed at only part of the problem is likely to be incomplete. There are also issues relating to the geometric special orientation of the nucleus replacement material, as well as the potential for later extrusion or displacement of the inserted material.

An approach to total disc replacement is disclosed in U.S. Pat. No. 6,419,706 which describes a cylindrical cage designed to screw into the endplates above and below the disc space. It is composed of a metal shell that is divided in two mobile upper and lower halves for anchoring into the endplates. This metal jacket surrounds a flexible core. The core is a "viscoelastic" material—suggestions include a silicone polymer. This design could be inserted using a posterior approach in the same manner that cages filled with bone graft material are placed when a spinal fusion is the desired outcome. The problem of extrusion of the central core is an issue, as is the shortcomings associated with a cylindrical implant. Typically these devices require more retraction and therefore potential injury to the neural elements, particularly when a large size is required due to a large disc space with preserved height. This is in contrast to more rectangular shaped implants, where height can be increased without increasing width. The other unavoidable aspect of the screw in cylinder design is the destruction of the endplates necessitated by the action of the screw threads. This could result in subsidence of the implant with subsequent collapse and narrowing of the disc space over time with attendant loss of motion.

U.S. Pat. Pub. Nos. 2006/0085073 and 2006/0085074 reveal a device intended to replace not only the entire disc but also both paired facet joint. It contemplates a biocompatible thermoplastic polyurethane or high performance nylon "balloons" inflated with a fluid in a closed hydrodynamic circuit. There is a fluid connection not only between the rod-like balloons attached to the pedicle screws, but also with the inflatable or expandable element filling the disc space. Loss of pressurization over time is an obvious concern with respect to that design.

In U.S. Pat. Pub. No. 2006/0085076, there are paired implants placed from a posterior direction on either side of the disc space. Each disc implant is composed of two components, which mate with one another by employing a shallow asymmetrical ball and socket design, which permits some translation as well as flexion and extension between the two components. Each component is secured to the underlying vertebral endplate with a single angled screw with a recessed head. It is stated that the surface of the prosthesis can be provided slightly roughened so as to increase bonding of the same with bone and/or one or more surface coatings can be provided thereon, such as for example, hydroxyapitite or plasma spray. The posterior elements replacement device is a telescoping arch which is anchored to pedicle screws. The sliding members articulate somewhat loosely which allows for "small degrees of rotation and side to side flexion." This design gives the illusion of bending as the rod lengthens. Problems with this design include the potential for posterior extrusion of the implant. Each half of the paired device is secured only with a single bone screw. Additionally there is little to prevent dislocation of the shallow ball and socket articulations.

U.S. Pat. Pub. No. 2005/0283247 discloses a design for posterior artificial discs with the ability to expand the implant after it is inserted into the disc space. A single banana or boomerang shaped implant is used rather than two symmetrically paired devices. The expansion is achieved by a number of different options, including a cam shaft design which permits sequential distraction by turning a screw mechanism built into the side of the device. In some of these embodiments it appears that the expansion may not be readily reversible. The disc replacement prosthesis is intended to be used in conjunction with a posterior dynamic stabilization system replicating the function of the facet joints. The elongated member connecting pedicle screws is constructed to allow for movement within the pedicle screw heads as well as a ball and socket joint at the midpoint of the rod, which allows for bending at that point. The mobility at the pedicle screw heads is permitted by wiggly attachments, either by a mismatch between the size of the pedicle screw heads and the rod, or by a mismatch between the screw heads and a receiving hole in the flat plate-like terminus of the rod. It is not disclosed that the rod-like member has the capacity to elastically increase in overall length. An increase in the distance between pedicle screw heads is essential if spinal flexion is to occur in a relatively normal fashion with an anteriorly located instantaneous axis of rotation. An additional potential issue is the difficulty of placing a single implant of this shape in the exact center of the disc. Perhaps of even greater concern is the potential for dislocation between the upper and lower element at the ball and socket articulation. It is stated that in some embodiments an "elongated member" may couple the upper and lower elements.

Another expandable design is disclosed in U.S. Pat. Pub. No. 2005/0261769. Two metal shells are jacked open and apart using a gear mechanism. Several options for the core element situated between the metal shells are discussed. A drawback with all of these options is the difficulty that would be encountered in removing the device, should revision and extraction ever be required.

Since posterior placement is preferable to anterior placement, a need exists for a posterior disc replacement implant device that can be securely positioned without risk of displacement or migration. The device should replicate the primary functions of the disc allowing for flexion, extension, and modest rotation. Furthermore the device should be removable in a safe manner, facilitating replacement or revision surgery if it should be required.

It is anticipated that the patient's facet joints will be either partially or totally removed in preparation for implantation of the invention into the disc space. This is required in order to avoid excessive traction or damage to the nerve roots during insertion of the invention, and to permit placement of the attachment shaft in a location distant from the nerve roots. For this reason the device according to the invention is best used with dynamic spinal stabilization system or devices.

Dynamic spinal stabilization system or devices augment the existing joints of the spinal motion segment by providing additional strength and support by some form of mechanical resistance. The objective is to permit some motion within a physiologic range, yet relieve the symptomatic painful joints of a portion of the physical stresses. The symptoms are improved as the device shares some of the load placed on the spine and protects against excessive or abnormal motion. Additionally some authorities believe that dynamic stabilization reduces the probability of accelerated degenerative changes on adjacent motion segments. Hopefully pain is lessened, flexibility is preserved and future problems at neighboring motion segments are reduced. The dynamic stabilization system can also be used in combination with a joint replacement device.

Spinal deformity is another potential application for dynamic stabilization. Scoliosis, or abnormal curvature of the spine, causes a rotational and side bending of the spine resulting in an abnormal shape and contour of the involved areas. Traditionally a spinal fusion operation is performed in an attempt to correct the curvature. An alternative approach is dynamic stabilization.

Many types of spinal stabilization devices are known. In U.S. Pat. No. 4,448,191 a flat metal band of titanium alloy is attached to the side of the spinous processes to exert a chronic dynamic corrective force to reduce the rotational as well as the lateral deformity of scoliosis. A method utilizing flexible rods of stainless steel is described in U.S. Pat. No. 4,697,582. Here the rods are also attached to the base of the spinous processes, and the guidance attachments allow axial movement of the rod permitting longitudinal spinal growth.

A similar concept for allowing the sliding of long rods either caudally or cranially is shown in U.S. Pat. Pub. No. 2004/0143264 which utilizes sleeves. A design employing springs is provided in U.S. Pat. No. 5,672,175. In this design two rods are attached to the spine with pedicle screws, with compression resisting springs on one side and extension resisting springs on the other side. The rods are fixed at the midpoint of the deformity but can slide through the connectors at either end—enabling longitudinal growth as well as rotation about any horizontal axis. This design also contemplates electronic micromotors to enable adjustment in the tension by moving the position of a stop. A device placed anterior to the spine is described in U.S. Pat. No. 6,296,643. Plates are positioned along the front of the vertebral bodies using bone screws. These plates are then connected using a cable, synthetic ligament, or flexible rod.

Axial joint pain resulting from degenerative changes in the spinal motion segment is difficult to treat. Sometimes dynamic stabilization is employed as a stand alone strategy. The concept is that by sharing some of the load, the device relieves the spinal joints of stress and thereby reduces symptoms. Some designs rely on the presence of intact and preserved anatomic features of the vertebra, such as the midline spinous process arising from and projecting back from the lamina of the vertebra. One of the older and simpler concepts is disclosed in U.S. Pat Pub. No. 3,648,691. A flat strip is clamped to several spinous processes. A flexible non-toxic material such as vinylidene fluoride was stated to be preferable to cast or machined metal straps. In U.S. Pat. No. 5,011,484 a plastic insert is described which fits over and between the spinous processes to restrict but not entirely prevent movement. The suggested material is polytetrafluoroethylene with a low friction coefficient to facilitate the sliding of the spines of the vertebrae inside the inserts. A semi-flexible intraspinous block is described in U.S. Pat. No. 5,609,632. This design also contemplates a flexible ligament composed of Dacron® (polyethylene terephthalate) wrapped around the spinous processes. In U.S. Pat. No. 6,440,169 a titanium alloy leaf spring is placed between the spinous processes, with one variation including a solid core of a viscoelastic material such as polyurethane or silicone.

Another device mounted on the spinous process is detailed in U.S. Pat. Pub. 2002/0095154. This is a design consisting of a compression spring, with another embodiment utilizing a piston/cylinder design and a flexible housing with a gas or liquid working the piston instead of the spring. All of these devices depend on intact spinous processes, and cannot be used when these structures are small or have been surgically removed.

In U.S. Pat. Pub. No. 2006/0084991 a design is presented which is also envisioned to be positioned in part between existing spinous processes, although the inventors state it can also be implanted after laminectomy and removal of the spinous processes. Transverse rods are contoured and bent toward one another to permit location between the spinous processes and also to allow for placement of an articulating joint and/or a central spacer between the two transverse rods. In addition, elastic elements are used to further join together the transverse rods. It is suggested that the elastic elements could be preferably formed from a biocompatible polymer, such as polyurethane, composite reinforced polyurethane, silicone, or other materials.

Another approach to strengthening the spine yet preserving motion is the use of artificial ligaments. The use of a flexible ligament made from Dacron® attached between pedicle screws is presented in U.S. Pat. No. 5,092,866. A more complicated design also intended for use between pedicle screws is described in U.S. Pat. No. 5,180,393. Braided multifilament yards of retractable polyester are arranged in two separate layers: a longitudinal primary layer in a figure-of-8 pattern covered by a transverse secondary winding. The first layer resists extension and the second layer resists compression. Other concepts include the notion of augmentation of the anterior longitudinal ligament in the front of the spinal column. A synthetic anterior longitudinal ligament composed of ultra-high molecular weight polyethylene in the form or a single strand, cable, tube, or patch is presented in U.S. Pat. Pub. No. 2002/0107524. A mesh design is proposed in U.S. Pat. Pub. No. 2002/0120269, with a variety of metal or fiber materials suggested as options. A wide range of possibilities mostly involving anterior flexible bands was revealed in U.S. Pat. Pub No. 2002/0120270. Cross coupled bands between pedicle screws in an "X" pattern to help prevent rotational forces on facet joints, used in association with flexible "dampers" attached to pedicle screws, were disclosed in U.S. Pat. Pub. No. 2002/0133155. Although some flexibility may be permitted by these ligament inventions, elongation is generally prohibited by these designs due to the inherent lack of elasticity.

Solid flexible members positioned between pedicle screws is another design consideration. A flat or oval flexible strip composed of carbon fiber reinforced plastic is described in U.S. Pat. Nos. 4,743,260 and 5,282,863. A variety of polymers are suggested, and manufacture using a replamineform process is recommended. This results in porosity of the strip, and it is anticipated that fibroblasts will grow into these porosities, augmenting its fixation but preserving the flexibility. A solid flexible rod composed of aromatic polycarbonate-polyurethane based material such as Bionate® or Chrono-Flex® is suggested in U.S. Pat. Pub. No. 2003/0220642. A titanium rod divided by a flexible joint made of "organic silicone compounds" is described in U.S. Pat. Pub. No. 2004/0049189. In U.S. Pat. Pub. No. 2003/0171749, the central portion of the rod is divided in half lengthwise. Bending of the rod is permitted only along the sagittal plane dividing the bifurcated area, thus limiting bending in other planes. Several flexible rod-like members constructed from hollow tubes with slits cut in a spiral pattern are presented in U.S. Pat. Nos. 6,986,771 and 6,989,011. Two or more tubes with different spiral patterns are fit snugly one within the other. Tension bands attached to the side of the tubes can provide resistance to motion. Other embodiments include a solid central flexible rod, braided wire, flexible plastics and rubber based materials. All of these flexible straight strip, rod, and rod-like designs permit bending, but once again elongation of the flexible member is not possible. Another kind of solid flexible rod is disclosed in U.S. Pat. Pub. No. 2005/0277922, in which a molded rod composed of a compressible substance was surrounded by a molded material resistant to elongation. A large number of materials were suggested, including a rubbery polymer for the compression element and silicone-polyurethane for the tension element. It is unclear how much elongation and bending would result from this combination.

A straight and rather large diameter device for use as an elastic "damper" is shown in U.S. Pat. No. 5,540,688. This invention is constructed of a core material loaded in elongation, and a sleeve or jacket loaded in compression. Three embodiments are presented, and the materials suggested included a "bio-compatible elastomer." In contrast to other straight rod-like designs, this invention would permit elongation of the member. However, bending is prohibited, and flexion and extension of the spine apparently depends upon the function of a ball and socket articulation with the pedicle screws permitting free polyaxial movement.

A flexible "U" shaped rod is described in U.S. Pat. No. 5,415,661. Detailed manufacturing options are discussed and the preferred embodiment is identified as a carbon reinforced plastic. Specifically the carbon fibers are oriented in the optimal alignment and density using prepreg tapes, and net compression molding using polyetheretherketone as the polymer is employed. The design in the shape of a "U" would permit elongation between the pedicle screw heads, which is essential in permitting forward flexion of the spine with a relatively normal instantaneous axis of rotation. Unfortunately the design is impractical because of the physical space limitations in the operative field. The distance between the pedicle screw heads is quite small, especially between L5 and S1. Furthermore the anteriorly projecting "U" shape would impinge upon the posterior bony structures of the spine or the nerve roots. A similar concept involving a more complex "inverted T" shaped bend in a flexible rod is presented in U.S. Pat. No. 6,966,910, but suffers from the same limitations.

Various spring designs have been incorporated into inventions designed to preserve motion yet add support to the spine. An invention designed for use in the front of the cervical spine utilizes a series of leaf springs which resembles an accordion, and is revealed in U.S. Pat. No. 6,293,949. A shape memory alloy is suggested as material, and specifically nitinol is recommended. This is an alloy of titanium and nickel with a low corrosion rate, excellent wear resistance, and minimal elevations of nickel levels in the tissues in contact with the metal. The presence of vital vascular structures makes this device unsuitable for the anterior lumbar spine.

Several designs utilize springs with rod-like members in order to permit elongation and compression of the rod, often incorporating a piston and cylinder component. A relatively simple device is disclosed in U.S. Pat. Pub. No. 2004/0049190 in which a rod is surrounded by a spring. The rod is rigidly fixed to one pedicle screw, but sliding is permitted through the attachment to the other pedicle screw. The rod is coated with ultra-high molecular weight polyethylene to permit sliding. Either a compression or an extension spring can be used. Bending of the construct, however, is not allowed. A modification to permit both elongation and bending is disclosed in U.S. Pat. Pub. No. 2006/0036240. A spring is associated with a telescoping rod with a curved track. With elongation, one component of the rod slides along the curved track permitting an imitation of bending. A telescoping rod on a curved track without an associated spring is presented in U.S. Pat. Pub. No. 2006/0085076. The device is meant for use in conjunction with posterior artificial disc implants. This again permits elongation or shortening with the illusion of bending.

Another approach to the twin problems of achieving not only length variability but also flexibility is provided in U.S. Pat. Pub. No. 2005/0283247. This is designed for use with a posteriorly positioned artificial disc replacement device. The elongated member connecting pedicle screws is constructed to allow for movement within the pedicle screw heads as well as a ball and socket joint at the midpoint of the rod, which allows for bending at that point. The mobility at the pedicle screw heads is permitted by wiggly attachments, either by a mismatch between the size of the pedicle screw heads and the rod, or by a mismatch between the screw heads a receiving hole in the flat plate-like terminus of the rod.

In U.S. Pat. No. 7,029,475, the device employs compression springs in a telescoping piston system. This invention is adjustable so that maximum resistance to motion in elongation and shortening is achieved in the neutral zone. Outside of the neutral zone the resistance provided by the invention is less. Bending of the device is not possible, so in order to allow spinal flexion, special mobile articulations with the pedicle screws are required to permit active angular movement at the points of attachment.

Hydraulic circuits are yet another design concept. In U.S. Pat. Pub. No. 2003/0055427, a compression spring and a piston containing a hydraulic circuit with the reservoirs are placed in the disc space. Bending of the device is not permitted, so flexion and extension of the spine once again apparently depends upon the function of a ball and socket articulation with the pedicle screws permitting free polyaxial movement. Yet another design envisioning the use of a complex hydraulic circuit is disclosed in U.S. Pat. Pub. Nos. 2006/0085073 and 2006/0085074. Inflatable elongated members composed of a type of biocompatible thermoplastic polyurethane are attached to the spine via pedicle screws. These fluid filled rod-like elements are connected through a closed hydraulic circuit to another inflatable element having the shape of and taking the place of the intervertebral disc.

An attempt to attain flexibility along with the potential for lengthening and shortening is described in U.S. Pat. Pub. No. 2003/0220643. Such a device would not depend upon complex moveable articulations with the pedicle screws. Several options are discussed. One embodiment contains two concentric springs separated by a rigid or semi-flexible tube. Another embodiment is an elastic cord surrounded by the extension block tube. Yet another variation discloses a telescoping flexible tube containing a spring, with the tube composed of a shape memory alloy such as Nitinol, or polyethylene. These designs share the common goal of allowing bending and elongation with a stretchable element, but preventing buckling of the stretchable element with a surrounding tube.

SUMMARY OF THE INVENTION

The lumbar disc replacement implant is designed to fit in the disc space with the upper and lower surfaces corresponding to the lens or lozenge silhouette of the disc space found therein. This overall shape is also advantageous for insertion of the implant into the disc space. The outline of the implant device according to the present invention can approximate the outline of implants currently in common use that are designed for posterior interbody fusion. The intended purpose of the implant according to the present invention is to preserve mobility between the spinal bones, rather than to result in a bony fusion between them. As a result of the design, the upper and lower surfaces of the implant are preferably closely approximated to the endplates of the vertebral bodies on either side of the disc space.

A portion of the implant is fabricated with an anchor shaft which extends out of the disc space in a manner to allow the anchor shaft to attach directly to the spine by pedicle screws or to a rods attached to spinal stabilization device or devices. The anchor shaft can extend or project out of the disc space in a generally perpendicular orientation to the vertical plane of the disc space or in an angular fashion from the vertical plane of the disc space. The lower half of the implant can be firmly fixed to the lower vertebra by means of a connection between the anchoring shaft and a pedicle screw, which placed in the pedicle of the lower vertebra. This connection can occur directly to the anchoring shaft. Alternatively this connection can occur indirectly through known intervening coupling mechanisms or spinal stabilization devices which are connected to the vertebra by a pedicle screw. Some such stabilization devices, connecting devices and equipment can be obtained from well known medical suppliers such as SCIENT'X USA.

The lower half of the implant may also have projecting fins or ridges in order to further stabilize the lower half with respect to the inner surface of the endplate of the lower vertebra. The upper mobile half of the implant is embedded in the undersurface of the endplate of the upper vertebra as a result of small projections or tooth like protuberances. The upper half of the implant is mobile and can slide up and down as well as experience small side to side movements with respect to the lower half of the implant. As a result motion between the two vertebrae is facilitated.

According to the present invention, the implant may be fabricated from any suitable biocompatible metal such as stainless steel or titanium or titanium alloy. It may also be constructed in whole or in part from any suitable non metal material, a non limiting example being polyetheretherketone PEEK. Gliding surfaces may be fabricated from, or coated with, any suitable biocompatible material with a low coefficient of friction. A non limiting example is ultra high molecular weight polyethylene UHMWPE. Additionally, those surfaces designed for contact with bone may be roughened and coated with substances engineered to encourage in growth of bone at the implant/bone interface. The width of the implant can be approximately 10 mm and the length can be approximately 22 mm or any workable length and width less than the patient's disc space. The total height of the upper and lower implant can be approximately 12-16 mm or a height less than or equal to the disc space.

In one embodiment of the invention, the mobility between the upper and lower implant is achieved by means of a guide rail on the lower implant. This embodiment allows sliding of the mobile component along the length of the guide rail. The mobile component is in firm contact with and is embedded into the inner surface of the endplate of the upper vertebra. The guide rail is preferably contoured in an arc shape, which replicates the normal instantaneous axis of rotation as the upper vertebra moves relative to the lower vertebra. The opening of the central channel in the sliding member is cut slightly larger than the guide rail in the anterior aspect of the channel. This somewhat loose fitting permits some side to side motion as well. The individual components of the implant are modular, and can be assembled prior to insertion so the device can be implanted together. Another option allows for sequential placement in the disc space with the pieces locking in place. In either technique, the overall assembly is firmly fixed in position by means of direct or indirect connection between the anchor shaft and the pedicle screw.

In this embodiment, these implants are preferably used in pairs, one on either side of the disc space. Sliding of both of the upper implants of the paired implants can occur in the same direction permitting either flexion or extension of the spine. Alternatively, sliding of the upper implants can occur in opposite directions permitting some rotation of the upper vertebra in relation to the lower vertebra. Precise positioning of these paired implants within the disc space is not required. This differentiates the device according to the present invention from those implants designed for implantation using a transabdominal or anterior approach. The essential aspect of placement for the paired posterior implants is that the long axis be located in the sagittal plane of the spine. While symmetry with respect to the absolute center of the disc of the paired implants is desirable, it is not mandatory. Furthermore, it is anticipated that the facet joints will be either partially or totally removed in preparation for implantation of the invention into the disc space. This is required in order to avoid excessive traction or damage to the nerve roots during insertion of the invention, and to permit placement of the anchoring shaft in a location distant from the nerve roots. For this reason the implant according to the invention is preferably intended for use with known spinal dynamic stabilization systems or devices.

In another embodiment of the implant, the mobility between the upper and lower halves of the implant is achieved by virtue of a slot or groove with a corresponding tongue in a slidable tongue and groove joint. The tongue on the upper mobile half of the implant articulates with slotted groove on the lower fixed half. The surface of each is preferably contoured in an arc shape, so that when sliding occurs of the upper half in relation to the lower half, the trajectory of motion replicates the normal instantaneous axis of rotation of the vertebrae. In this design, the movement is controlled through a tongue and groove mechanism rather than a guide rail and channel design. The individual components of this embodiment are modular, and can be assembled prior to insertion, or can be placed in the disc space sequentially with the pieces locking in place. The overall assembly of this embodiment is firmly fixed in position by means of either direct or indirect attachment to the pedicle screw in the lower vertebra. The connection occurs between the pedicle screw and the anchoring shaft, which arises from the posterior fixed component of the invention and projects out of the disc space.

In this embodiment as well, these implants are preferably to be used in pairs, one on either side of the disc space. Sliding of the upper implants can occur in the same direction permitting flexion or extension. Alternatively, sliding of the upper implants can occur in opposite directions permitting some rotation of the upper vertebra in relation to the lower vertebra. Slight variability between the dimensions of the tongue and groove can achieve some side to side movement.

Furthermore it is anticipated that the patient's facet joints will be either partially or totally removed in preparation for implantation of the invention into the disc space. This is required in order to avoid excessive traction or damage to the nerve roots during insertion of the invention, and to permit placement of the attachment shaft in a location distant from the nerve roots. For this reason the device according to the invention is intended for use with dynamic spinal stabilization system or devices. The preferred dynamic spinal stabilization system is described herein as the interconnected bullets nested in a spring nested in a sleeve of woven material connected to the spine by intermediary transverse rods.

In yet another embodiment of the implant, the front of the implant is rotatable relative to the back part of the implant. The anchoring shaft remains fixed in position and is attached to the lower vertebra through a connection with a pedicle screw in the lower vertebra. The rotation of the front part of the implant is intended to occur after the implant has been implanted at an angle to the vertical cross sectional plane of the disc space. This preferred insertion angle advantageously permits placement of the center of the implant into the center of the disc space and allows the attachment to the lower vertibra. The surgical technique for this placement, which occurs at a more lateral starting pointing further from the midline, is termed a transforamenal approach. This permits implantation of a larger implant, which is beneficial since the surface area of the upper implant in contact with the endplate of the upper vertebra will be correspondingly increased. The implantation can be facilitated by use of known surgical instruments and medical tools such as Crescent Instrument Set provided by Medtronic (www.medtronicspinal.com).

The rotational ability of this embodiment of the implant according to the invention is preferably provided by means of a gear mechanism. Rotation of the front half of the invention is accomplished after the entire assembly is implanted into the disc space, with the center of the rotation point at the center of the disc space. The gear mechanism is actuated by turning the head of a rod located at the base of the anchoring shaft, which is located on the fixed or immobile back half of the invention. Turning the rod turns a gear which meshes with a larger gear that is integrated into the base of the front half of the implant. As a result the orientation of the front half of the implant is changed, whereas the orientation of the back half of the implant remains unchanged. The objective of the rotation is to align the front half of the implant so that the long axis comes to lie within the sagittal plane, which is the plane in which flexion and extension of the spine occurs.

The front half of this embodiment of the implant according to the invention contains a sliding element. The movement of the sliding element is confined to a tract defined by a guide rail or post on the front half of the implant and the corresponding channel cut through the center of the sliding element. This tract has an arc shape, so that motion of the sliding element follows an arc like trajectory.

In another embodiment, a tongue and groove design is employed. Since the inner aspect of the endplate of the upper vertebra is attached to the sliding element by virtue of projecting ridges or teeth, the movement of the upper vertebra approximates the normal instantaneous axis of rotation in the sagittal plane. Therefore flexion and extension of the spine is permitted at the spinal motion segment implanted with the implant. Since the channel cut through the long axis of the sliding element is larger than the dimensions of the guiding rail or post, some side to side movement as well as slight rotation is permitted.

In contrast to the other embodiments, in this manifestation the implant is preferably intended to be employed as a single device implanted at each disc space, rather than used as paired implants as previously described. The implant can be of a larger size, which is possible due to the technique of insertion in a transforamenal approach. The transforamenal approach permits safe passage past the neural elements during insertion. Certainly, a transforamenal approach can be also be used for the paired implants, but it is mandatory with the single larger implant. Location of the single larger implant is optimal in the center of the disc, but it is not essential. The long axis of the front half of the implant should be rotated so that it is in the sagittal plane in order or allow for flexion and extension movements of the spine. This can be achieved even if the implant is not perfectly centrally located. Therefore placement of this implant is not as critical as those disc implants designed for anterior or transabdominal insertion.

Transforamenal posterior insertion of the single larger rotation-capable implant according to the invention requires surgical removal of the facet joint on the side of insertion. For this reason, the implant according to the invention is intended for use with known spinal dynamic stabilization systems. Bilateral or in some cases unilateral application of the dynamic stabilization system can be considered. When clinical conditions permit unilateral application, then a mini-open or expanded minimally invasive surgical procedure can be employed for insertion of the artificial disc and implantation of the dynamic stabilizing system.

An alternative method of use involves placement of a single non paired implant of the rotational post design embodiment together with unilateral placement of a posterior dynamic stabilization system. Since a one sided surgical exposure is required, implantation could potentially be accomplished using mini-open or expanded minimally invasive surgical technique. In that method, the facet joint, ligaments, and muscle tissue on the opposite side would be undisturbed. The inherent stability preserved as a result would justify and validate unilateral posterior dynamic stabilization. Hopefully, the smaller surgical exposure would be associated with a speedier recovery.

The implant can be used with a spinal stabilization system. The preferred spinal stabilization allows for flexibility and elasticity with resistance to buckling and avoidance of excessive buckling. One embodiment of the spinal stabilization device consists of interconnected bullets nested in a spring nested in a sleeve of woven fabric providing a flexible rod-like shape designed to resist excessive elongation and axial compression, prevent buckling and provide an absolute limit to elongation. Furthermore there is an advantageous bias with respect to the direction of bending, permitting some desirable control of spinal movement. It is designed for use with standard pedicle screw systems, and can be connected directly to the spine by the screws or indirectly to the spine by the screws via intermediary transverse rods.

The dynamic spinal stabilization device disclosed herein may be used in a stand alone application as a load sharing device for the spine, permitting movement within normal limits by what is termed dynamic stabilization. The dynamic spinal stabilization device disclosed herein may also be used at the end of a spinal fusion construct to reduce the problem of juxta-fusional breakdown. The dynamic spinal stabilization device disclosed herein may be employed in association with any disc replacement or disc augmentation technology.

The dynamic stabilization device is flexible in the midrange of elongation. However the dynamic spinal stabilization device becomes rigid when compressed, which prohibits buckling. At the limits of elongation, the dynamic spinal stabilization device also becomes more rigid. An absolute limit to elongation is provided.

Special means of articulation requiring mobile joint-like coupling mechanisms, either directly with pedicle screws or indirectly with transverse rods, are not required. In particular it is not necessary with the present invention to rely on mobile multi-directional articulations with the connecting elements. Standard poly-axial screws or other rigid and fixed articulations are sufficient. Because of this ability, several practical methods are available which allow for connection of multiple vertebrae in series if this is required by the clinical setting. An embodiment of the dynamic spinal stabilization device is composed of multiple components arranged in three distinct concentric layers or tiers, whose mutual interactions provide the desirable attributes of elasticity and flexibility but only within a safe and predetermined range. The tiers are nested one within the other. A cross-section of the dynamic spinal stabilization device according to the present invention would reveal the tiers arranged like layers in an onion or rings in a tree. The inner most tier consists of individual interlocking elements herein termed "bullets." The shape of the top and bottom sides of the interlocking bullet can be selected based on desired performance characteristics for the invention. For example, some designs permit flexibility primarily in only one direction or plane.

The bullets may be made of any suitable material such as titanium, a titanium alloy, stainless steel, and can be coated with a sliding material having a low coefficient of friction such as ultra high molecular weight polyethylene UHMWPE. Alternatively, the bullets may be made entirely of any suitable non metal material, an example of which would be polyetheretherketone (PEEK). The number of bullets comprising the inner most tier is variable and is determined by the desired length of the invention. The surgeon can select the most appropriate length at the time of surgical implantation. Within the inner most tier at either end of the series or stack of bullets are the attachment elements, which serve as attachment points for the invention with the spinal bones. The attachment elements will be composed of a suitable metal and designed to allow connectivity with existing pedicle screw systems, or alternative articulating fasteners.

The second or intermediate layer is composed of a spring. In one of the embodiments, an extension spring is utilized, which is designed to resist elongation. The spring may be composed of any suitable shape memory material such as a titanium alloy. The length of the spring in its resting form is chosen so that the individual bullet elements are fully interlocked with one another. This interlocking confers rigidity on the dynamic spinal stabilization device. When tension is applied to lengthen the spring, the individual bullet elements are no longer tightly locked, which allows for motion between them and confers flexibility on the invention. The shape and design of the interlocking section of the individual bullet elements influences the degree and direction of the flexibility that is permitted, as does the degree of separation between the bullet elements which is imparted by elongation of the spring. Graduated resistance to elongation is imparted by the elastic properties of the spring. The length of the stack of bullets determines the length of the spring, and the spring length is approximately the same as the length of the stacked bullets.

The third or outermost layer in the one embodiment is composed of a sleeve of material woven in the form of a Chinese finger trap, also known as a Chinese finger puzzle. The material used could be of any suitable material including but not limited to braided cable of titanium, titanium alloy, stainless steel, or a biocompatible non metal such as polypropylene, nylon, or other woven fabric. In the resting or non elongated state of the spring, this outer tier is characterized by a sleeve of fabric of a loose weave pattern. As the spring is stretched and elongated, the weave pattern tightens and the diameter of the outermost tier constricts around the spring in the intermediate layer.

This constriction confers rigidity on the stabilization device in the elongated state, and the weave pattern is designed so as to provide an absolute limit on the elongation of the invention at the desired maximum length. In this fashion, the outermost tier provides some rigidity at the maximum length as well as a positive stop preventing overstretching of the spring.

In the combined interactions of the three tiers or layers, the invention provides rigidity in the non elongated state, permits bending and flexibility which increases with stretching, but also establishes a safety limit and confers some rigidity which is reacquired at the maximum permitted elongation. The woven fabric is approximately the same length as the spring. Another embodiment of the dynamic spinal stabilization device is characterized by a fourth layer or tier comprised of a compression spring, designed to resist shortening of the interlocking bullets. In this embodiment, the layers or tiers alternate between metal and non metal composition, reducing friction and metal wear particle accumulation. In the neutral or resting state of the invention, the extension spring of the second layer is preloaded in a slight amount of elongation by the force of the compression spring in the fourth layer. With active compression of the invention, caused by spinal extension or backwards bending of the spine, the individual bullet elements of the innermost tier are interlocked and rigidity is conferred upon the invention. In this embodiment, some degree of flexibility is present in the invention in its resting or neutral state.

In yet another embodiment of the dynamic spinal stabilization device, each of the individual bullet elements of the inner most tier has a curved shape. This results in an overall curved shape of the stacked bullets. This curved shape can correspond to the normal and natural contour of the lower spine, which is termed lumbar lordosis. With the curved shape, the stabilization device provides the possibility for percutaneous or minimally invasive, surgical implantation of the invention. This could be accomplished utilizing existing commercially available instrumentation systems. During minimally invasive placement, increased rigidity of the stabilization could be temporarily or permanently conferred utilizing a central guide wire, which can be withdrawn after the invention is successfully positioned within the pedicle screws.

BRIEF DESCRIPTION OF THE DRAWINGS

FIG. 29 shows a side perspective view of the dynamic spinal stabilization device's inner most or first layer in a state of elongation at greater than maximum length;

FIG. 30 shows a side perspective view of the dynamic spinal stabilization device's middle or second layer of the invention in a state of elongation at greater than maximum length;

FIG. 31 shows a side perspective view of the dynamic spinal stabilization device's outer or third layer in a state of elongation at greater than maximum length;

FIG. 38 shows a cross-sectional view of the inner or first layer of the dynamic spinal stabilization device in a resting state of minimal length;

FIG. 39 shows a cross-sectional view of the inner or first layer of the dynamic spinal stabilization device in a state of elongation and flexible bending;

FIG. 40 shows a cross-sectional view of the inner or first layer of the dynamic spinal stabilization device with individual bullet elements of a design shown in FIG. 8 seen in a resting state of minimal length;

FIG. 41 shows a cross-sectional view as in FIG. 40 but in a state of elongation and flexible bending in the permitted direction;

FIG. 42 shows a cross-sectional view as in FIG. 40 also in a state of elongation but with only slight flexible bending in other than the permitted direction;

FIG. 43 shows a side view of the guide wire;

FIG. 44 shows a cross-sectional view of the inner or first layer of the dynamic spinal stabilization device composed of individual bullet elements similar to FIG. 40 but designed with a curved shape. The guide wire is seen inserted through a channel located in the center of the long axis of each curved individual bullet element;

FIG. 45 shows a cross-sectional view to FIG. 44 but with the guide wire removed, the invention in a state of elongation and flexible bending in the permitted direction;

FIG. 46 shows a cross-sectional view taken along line 46-46 of FIG. 45.

FIG. 49 shows a perspective view of an arrangement of multiple dynamic spinal stabilization devices connected to the spine indirectly via pedicle screws using intermediary transverse rods;

FIG. 50 shows a perspective view of paired plates for connecting the dynamic spinal stabilization device to either side of the spinous process of a vertebra;

FIG. 51 shows a perspective view of another embodiment of the paired plates for connecting dynamic spinal stabilization devices to either side of a spinous process of a vertebra;

DETAILED DESCRIPTION

Certain exemplary embodiments are described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1:
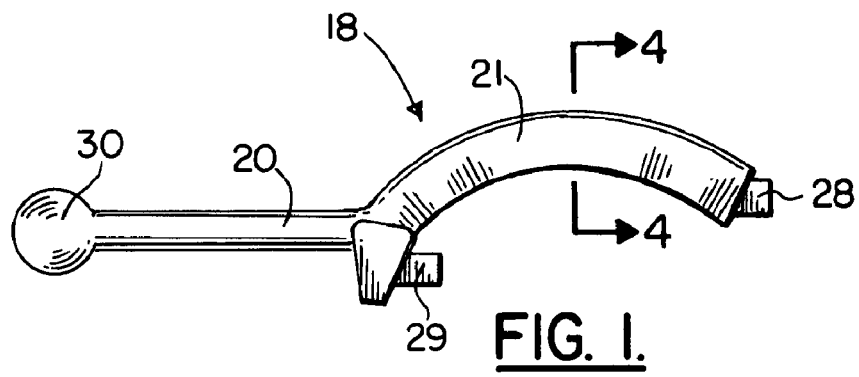
FIG. 1 shows a side view of the rail component of the implant.
Figure 2:
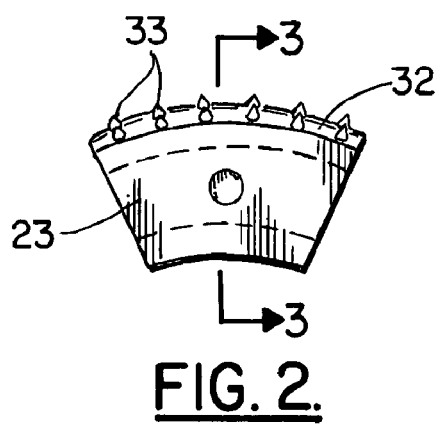
FIG. 2 shows a side view of the upper implant.
Figure 4:
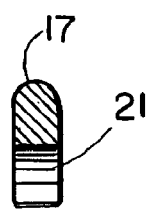
FIG. 4 shows a cross-sectional view along the lines of 4-4 of FIG. 1.
Figure 5:
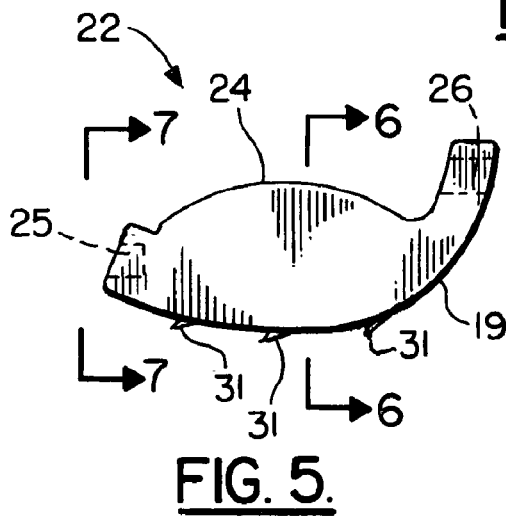
FIG. 5 shows a side view of the lower implant.
Figure 6:
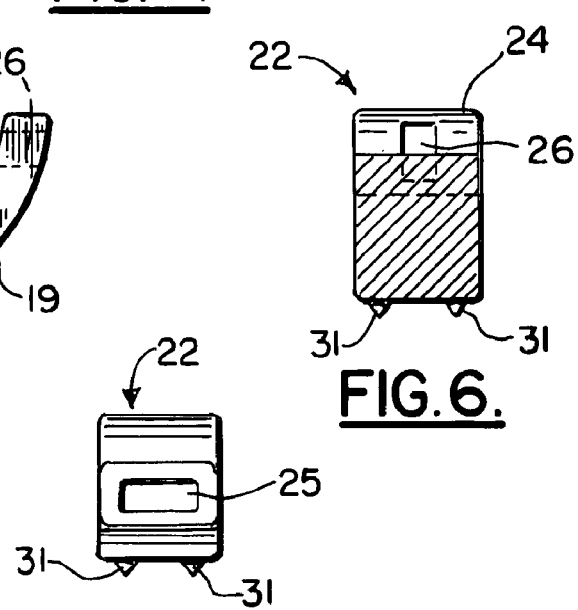
FIG. 6 shows a midbody side cross-sectional view of the lower implant along the lines of 6-6 of FIG. 5.
Figure 7:
FIG. 7 shows a cross-sectional view of the lower implant along the lines of 7-7 of FIG. 5.
Figures 8, 9:
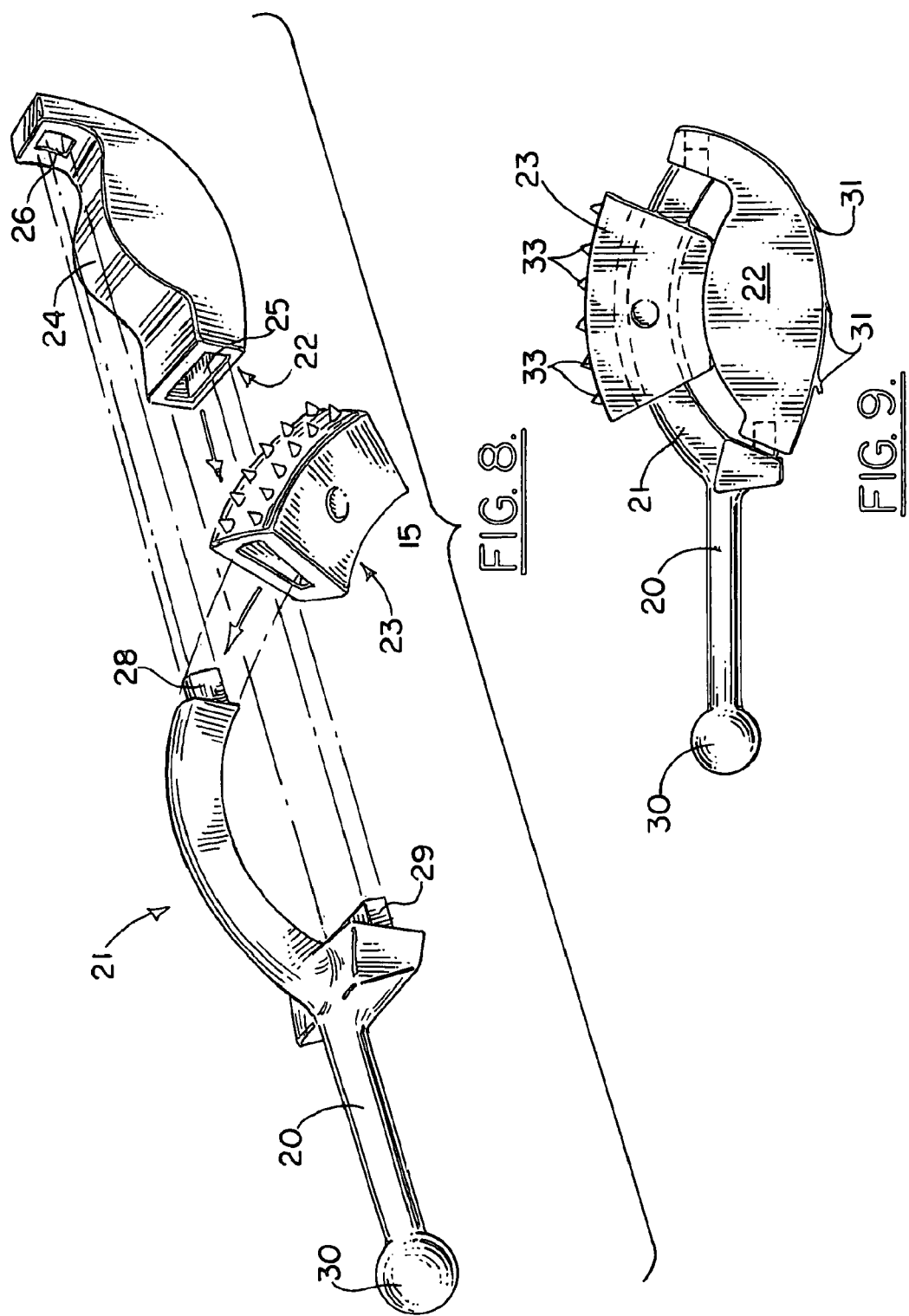
FIG. 8 shows a perspective view of the anchor rail embodiment showing the assembly.
FIG. 9 shows side view of the anchor rail embodiment of the assembled upper and lower implant.

The implant is presented in several exemplary but non limiting embodiments. The first embodiment is identified as the anchor rail design. It is comprised of 3 separate components, which fit together in a unified construct. In FIGS. 1-9 the individual components or elements are shown. In FIG. 1, the anchor rail 18 is composed chiefly of the anchor shaft 20 and the guide rail 21. The top 30 of the anchoring shaft 20 can be attached to known polyaxial articulating device similar to those found on multi-axial pedicle screws. The guide rail 21 preferably has a curved or scimitar design, and is thicker than it is wide. In one embodiment, it is constructed with slightly rounded ends 17 as shown in FIG. 4. In FIG. 5, the lower implant 22 is shown. The top surface 32 of the upper implant 23 has a curved shape corresponding to the inner surface 12 of the upper vertebral endplate as shown in FIGS. 12A-12F. The lower implant 22 is shown having a smooth dome shaped surface 24, which is intended to articulate with and support the sliding of the bottom surface of the upper implant 23. This articulation between the upper implant 23 and lower implant 22 provides additional support to the upper implant 23 so that some of the support and sliding stress is shared with the post 21. In FIG. 6, a front indentation or receptacle 25 on the lower implant 22, is designed to snugly and securely receive projections 29 located on the end of guide rail 21 and in FIG. 6, a back indentation or receptable 26 on lower implant 22 receives the midbody projection 29 on the guide rail and anchor post 18. On the bottom surface of the lower implant 22 are shown projecting fins or ridges 31, whose purpose is to further stabilize the lower implant 22 with respect to the lower vertebra. In FIG. 5 the contour of the lower surface 19 of the lower implant 22 is designed to match the contour of the inner surface of the lower vertebra upon insertion of the implant.

Figure 3:
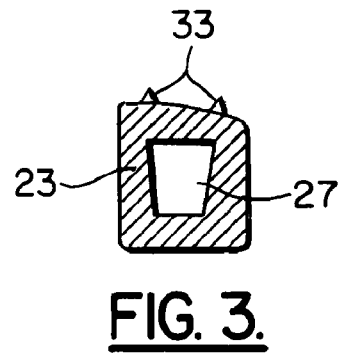
FIG. 3 shows a cross-sectional view of the upper implant along the lines of 3-3 of FIG. 2.

In FIG. 3, the upper implant 23 is constructed with a central cavity or channel 27, which is slightly larger in cross sectional diameter than the post 21. In one embodiment, the central channel 27 is trapezoidal in cross-section, permitting some side to side motion of the upper implant 23 with respect to the post 21. In FIG. 4, the cross section of the guide rail 21 shows the shape of guide rail. The top surface 32 of the upper implant 23 is designed to contour to the inner surface the upper vertebra having projecting fins or ridges 33.

In FIGS. 10 and 11 and FIGS. 12A-12F, a multi-step method is illustrated for the sequential assembly of the three separate components of the post design embodiment of the present invention performed within the disc space. Alternatively, this assembly may be completed outside of the disc space, and the three components 22, 23, and 18 inserted simultaneously after the dimensions of the disc space have been determined and prepared with progressive trial implants. The separate component design of this embodiment allows for implantation of a device of appropriate size, so that the device closely approximates and tightly binds with the inner surfaces of the endplates of the upper and lower vertebra on either side of the disc space. It is anticipated that the main variability in the assembly will involve selection of upper implants 23 of varying heights. This height variability will result in increasing or decreasing distance between the post 21 and the anterior surface of the upper implant 23. In this fashion, the upper implant of appropriate size can be chosen to insure a tight fit within the disc space resulting in optimum binding of the invention with the endplates with respect to the lower vertebra 38 and of the upper vertebra 39.

Figure 10:
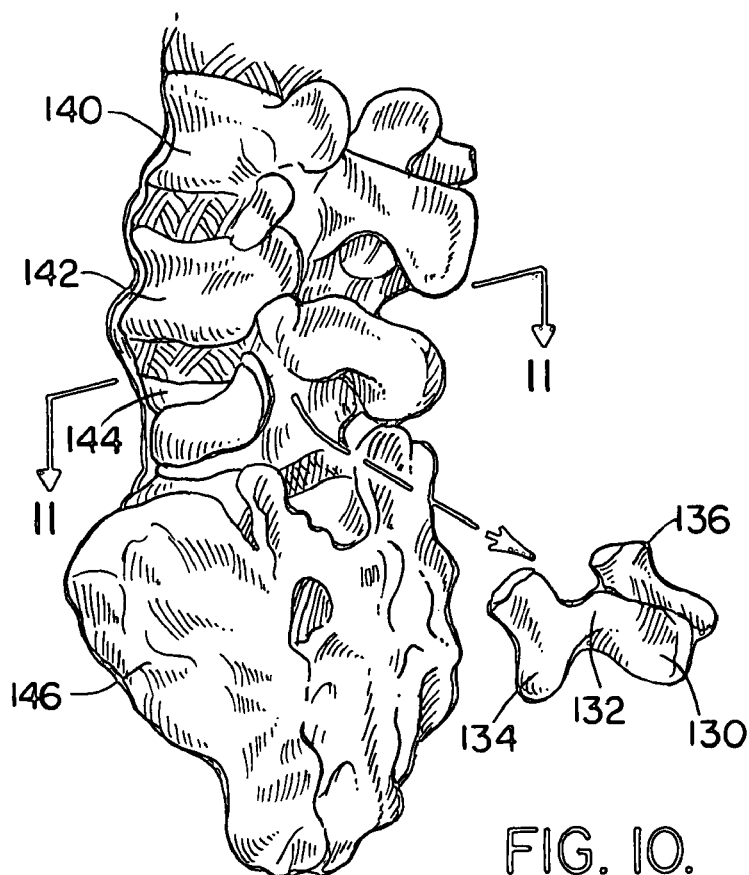
FIG. 10 shows a side view of a lower spine following surgical removal of the posterior vertebral elements.
Figure 11:
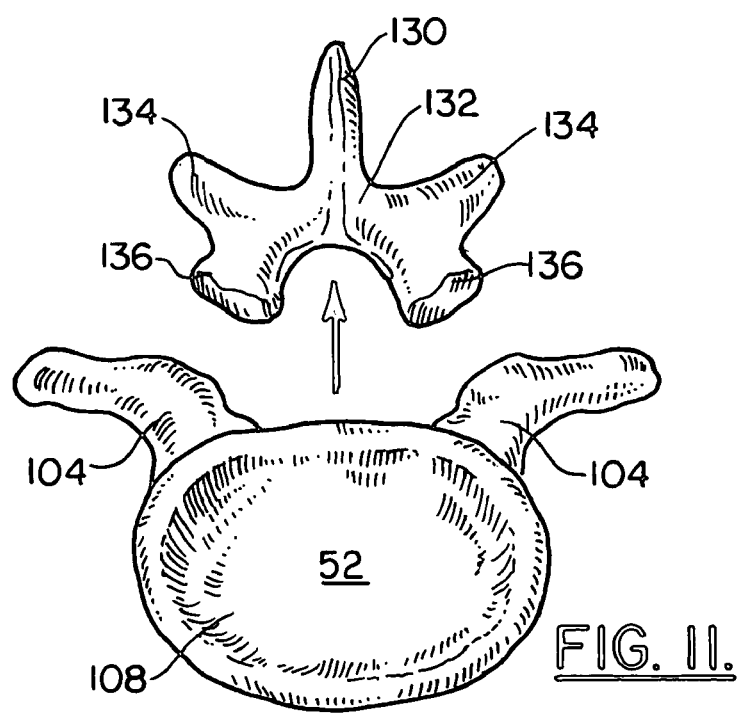
FIG. 11 shows a cross-sectional view of the vertebra along the lines of 11-11 of FIG. 10 following surgical removal of the posterior vertebral elements.
Figure 12A:
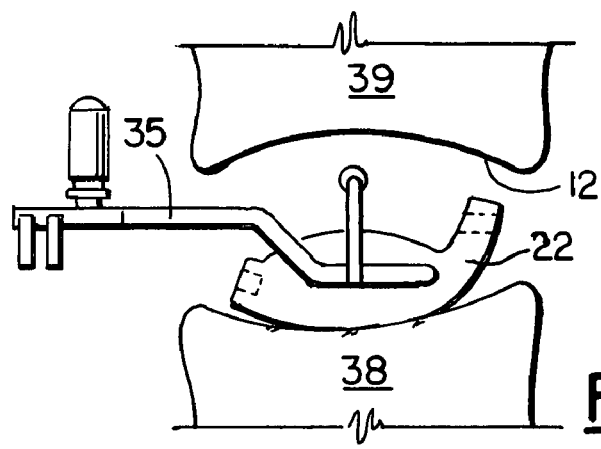
FIG. 12A shows a side view of placement of lower implant in disc space.
Figure 12B:
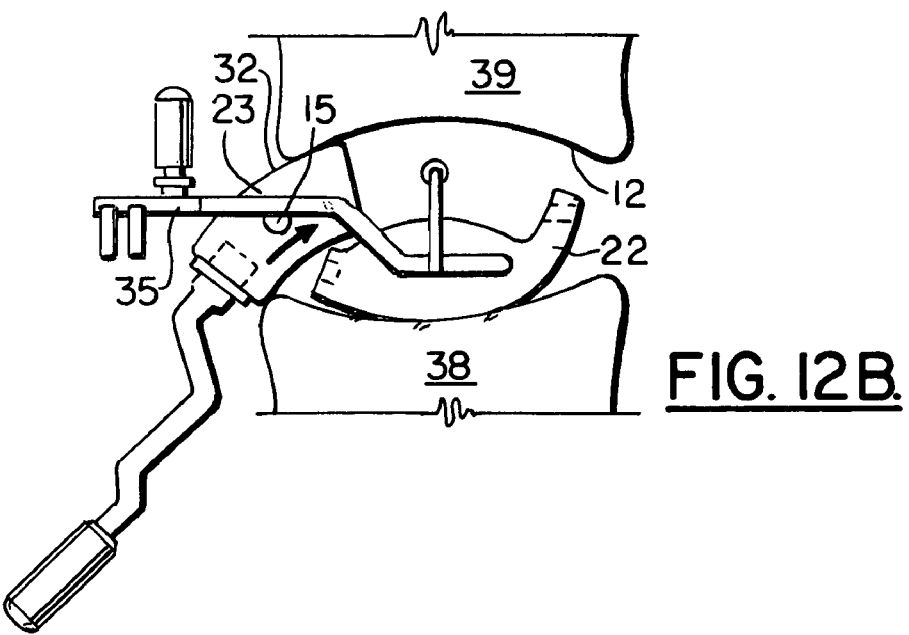
FIG. 12B shows a side view of placement of upper implant in disc space.
Figure 12C:
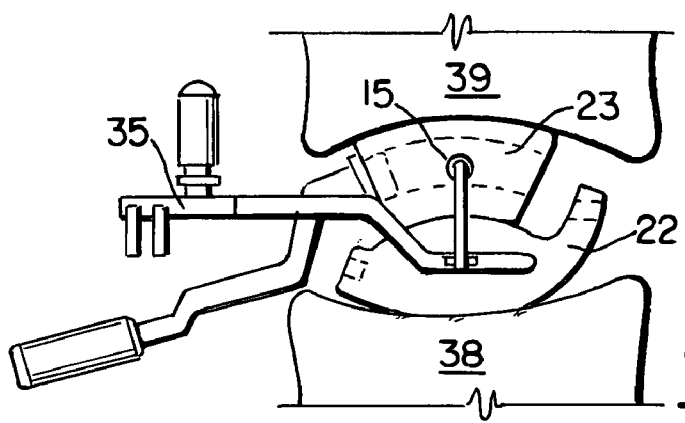
FIG. 12C shows a side view of placement of upper implant in disc space.
Figure 12D:
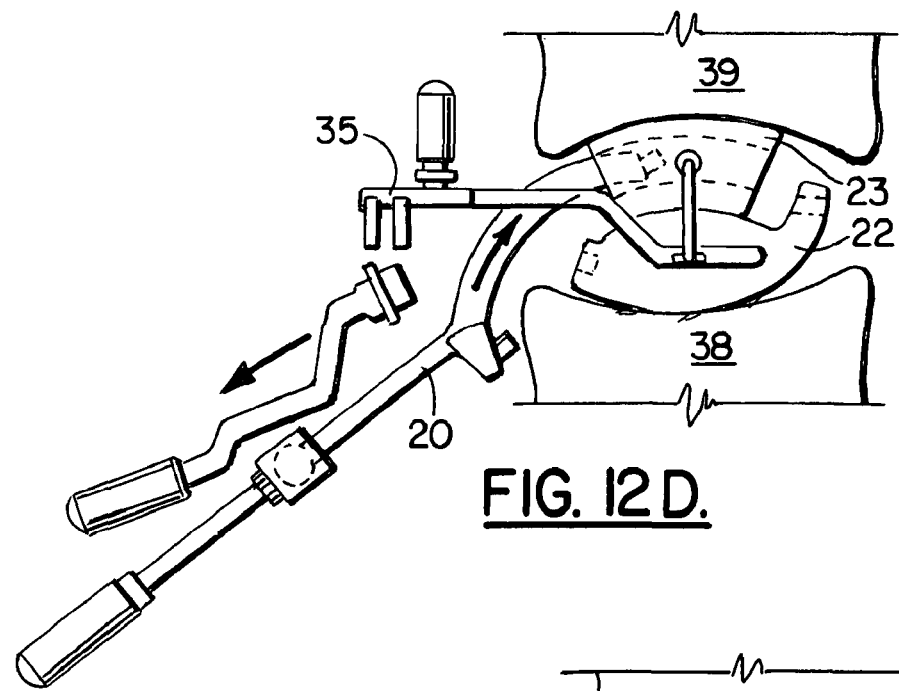
FIG. 12D shows a side view of placement of anchor rail in disc space.
Figure 12E:
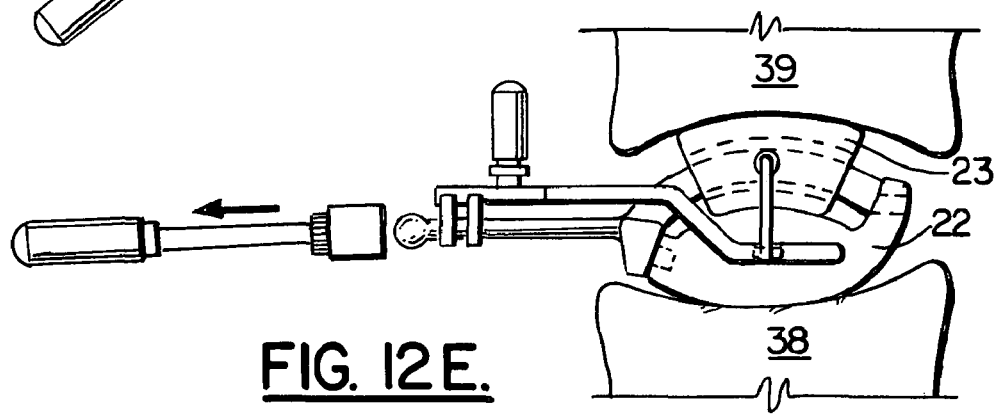
FIG. 12E shows a side view of placement of guide rail and anchor post within the upper implant in the disc space.
Figure 12F:
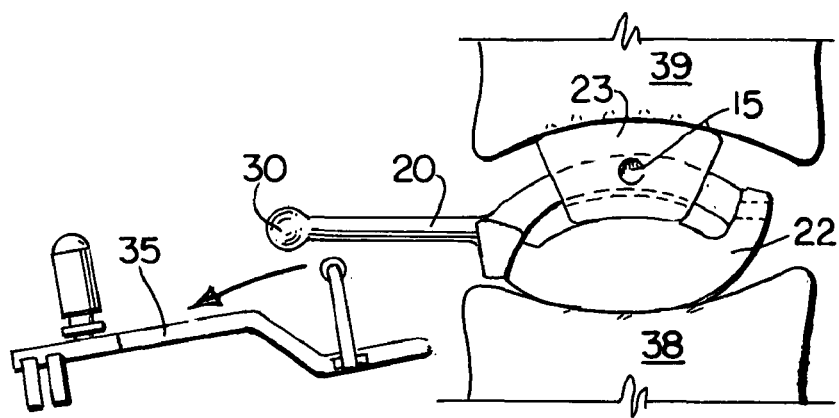
FIG. 12F shows a side view of completely assembled implant in disc space.

In FIGS. 10 and 11, the posterior vertebral elements, including the spinous process 130, lamina 132, inferior articulations process 134 and pars interarticularis 136 are surgically removed. The disc is next removed. Removal of the posterior vertebral elements is to provide access to the disc space and to minimize surgical trauma to spinal nerves. For sequential insertion of the anchor rail embodiment of the present invention, it is advantageous to place the lower implant 22 first, and the anchor rail 21 last. The upper implant 23 can be inserted together with the lower implant 22 or separately. The orientation of the spine and the upper implant 23 is maintained in neutral position, without flexion or bending of the spine during placement of the anchor rail 18. For placement, a holder/inserter tool 35, with side arms grasps the lower implant 22 as well as a portion 36 of the upper implant. The upper implant can have indentations 15 on its sides to facilitate grasping by the holder/inserter tool 35 also shown in FIG. 8 and FIG. 12C. Once assembly is complete, the holder/inserter tool 35 is withdrawn.

Figure 13:
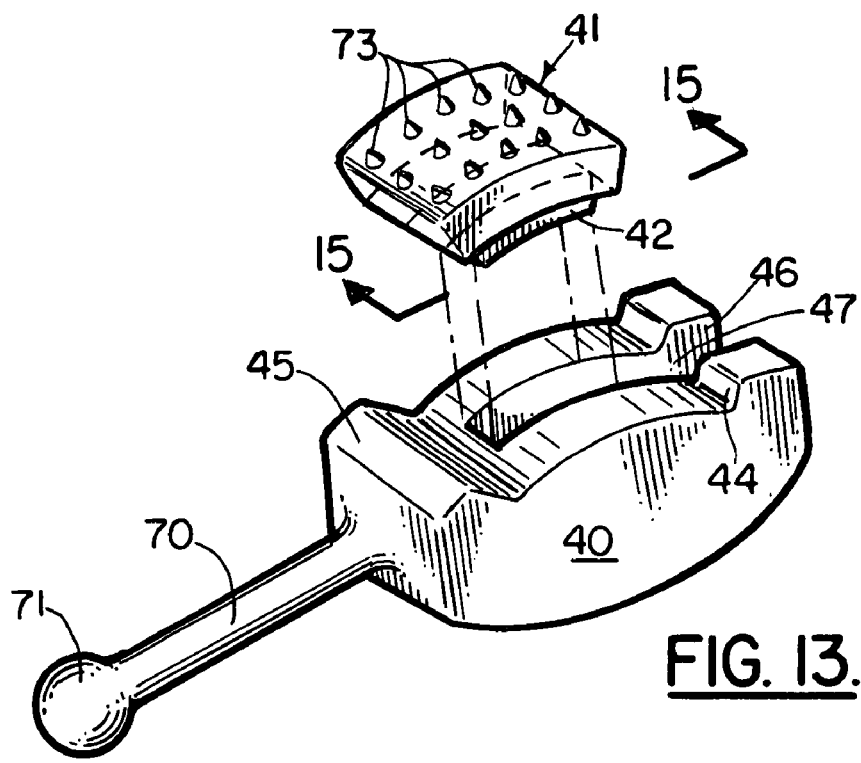
FIG. 13 shows a perspective view of the upper implant and lower implant of the tongue and groove embodiment.
Figure 14:
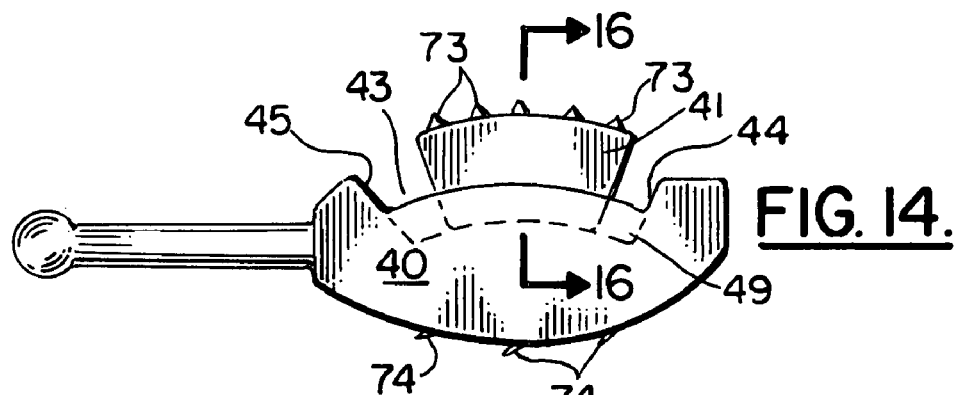
FIG. 14 shows a side view of the tongue and groove implant.
Figure 15:
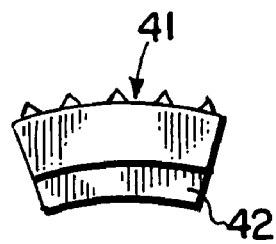
FIG. 15 shows side view of the upper implant.

Another embodiment of the present invention is termed the tongue and groove design, and is presented in FIGS. 13 and 14. The slot design is comprised of a slotted lower implant 40 and upper implant with tongue 41. The slotted lower implant 40 is attached to an anchoring shaft 70. The top 71 of the anchoring shaft 70 can be attached to the spine by known multi-axial articulating structures similar to those utilized on commercially available polyaxial pedicle screws available from surgical suppliers such as Medtronics and SCIENT'X USA (www.scientxusa.com). The upper implant 41 with tongue 42 articulates with the slotted lower implant 40 by means of a type of tongue 42 and groove 47 joint. The slotted lower implant 40 preferably has a curved surface 43 on which slides along the upper implant 41 with tongue 42. Slot 47 also preferably has a curved surface 72, corresponding to the curved surface of the end of the tongue 42. The front edge 45 and back edge 44 of the slotted lower implant 40 are shaped as positive stops. There can be a smaller positive stop 49 at the inferior aspect of the slot 47 since a partial continuation of the slot 47 is provided by inferior groove 46. The inferior groove 46 is designed to permit sequential assembly to the lower implant and the upper implant within the disc space. The positive back edge stop is provided by the outer surface of the back edge 44 and the back edge's smaller inner surface 49. The distance of approximately 2 cm between the positive stops 49, 44 and 45 on the top of lower implant 40 can limit the distance the upper implant slides and limit the amount of mobility between the upper and lower implant. The top surface of upper implant 41 has ridges or projection 73 for attachment to the upper vertebra and the bottom surface of lower implant 40 has ridges or projections 74 for attachment to the lower vertebra.

Figure 16:
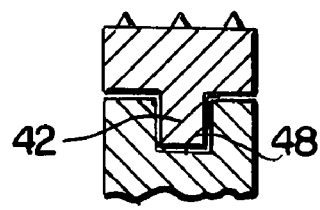
FIG. 16 shows a cross section view of the upper and lower implants with one embodiment of the tongue and groove joint along the lines of 16-16 of FIG. 14.
Figure 17:
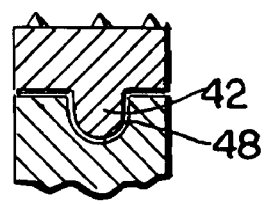
FIG. 17 shows a cross section view of the upper and lower implants along the lines of 16-16 of FIG. 14 with an alternative embodiment of the tongue and groove joint.
Figure 18A:
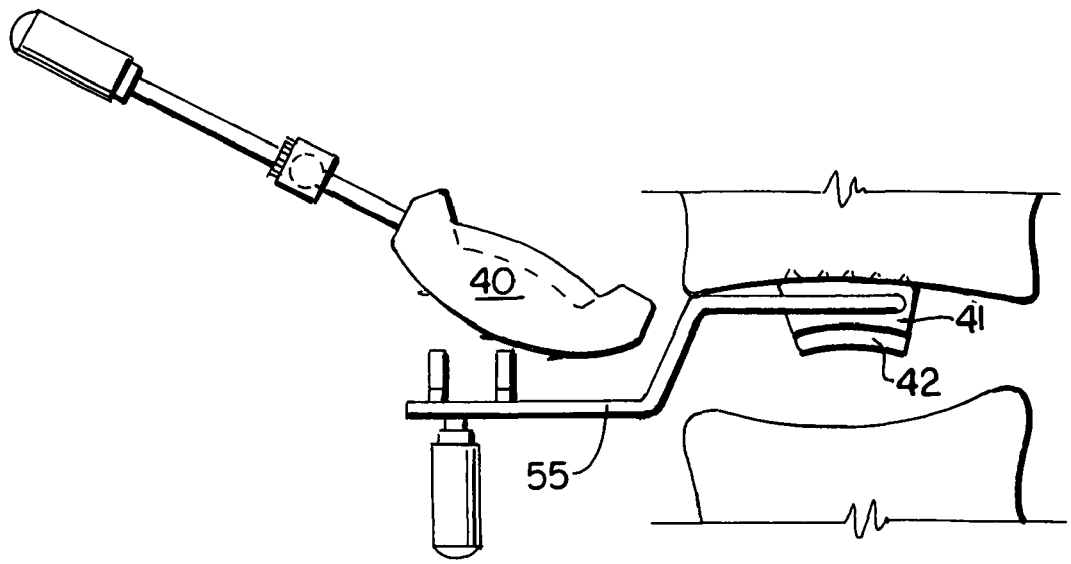
FIG. 18A shows a side view of placement of the upper implant of the tongue and groove embodiment in the disc space.
Figure 18B:
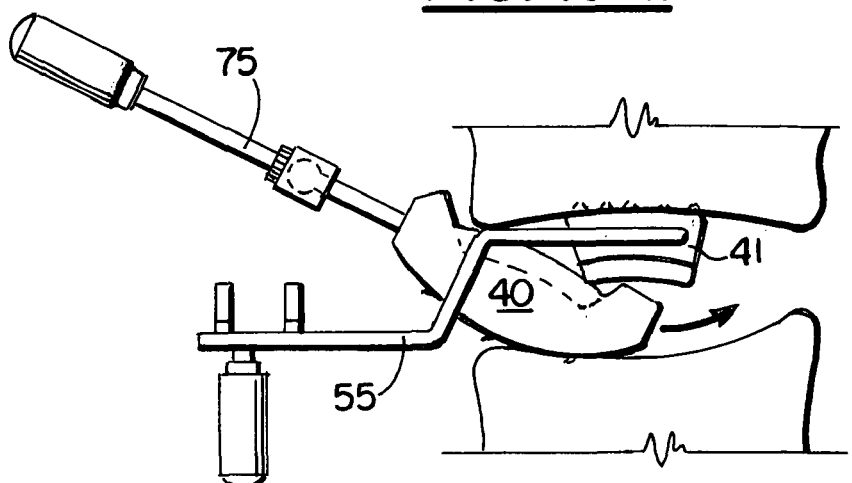
FIG. 18B shows side view of placement of the lower implant of the tongue and groove embodiment in the disc space.
Figure 18C:
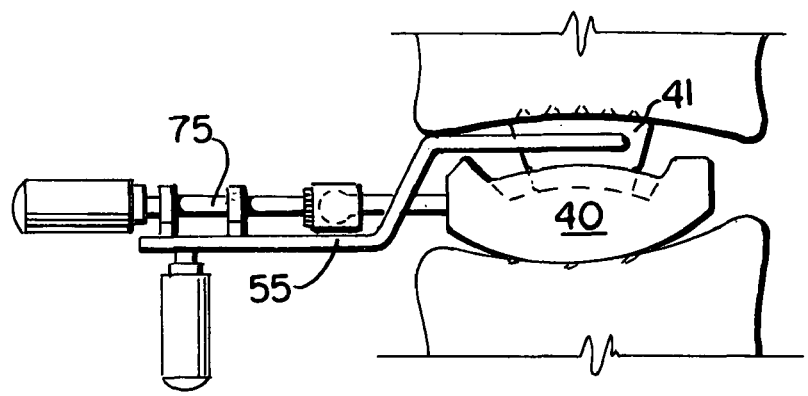
FIG. 18C shows side view of placement of the upper and lower implants of the tongue and groove embodiment in the disc space.
Figure 18D:
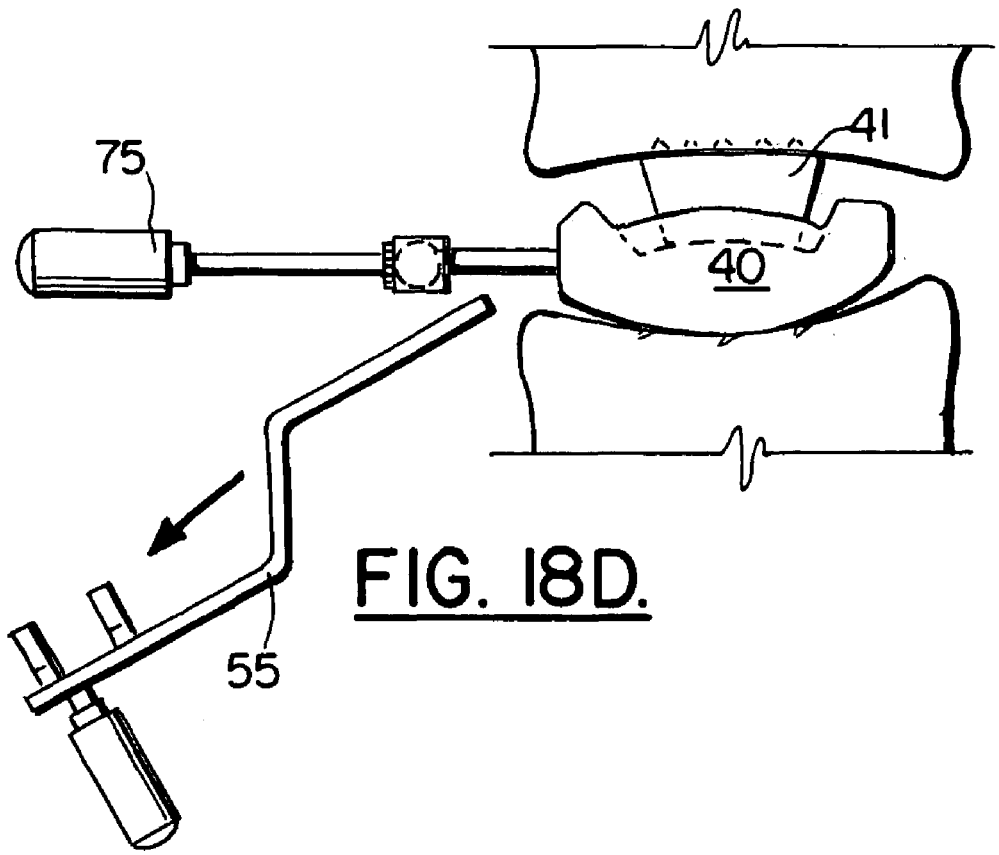
FIG. 18D shows side view of the assembled upper and lower implant of the tongue and groove embodiment in the disc space.
Figure 18E:
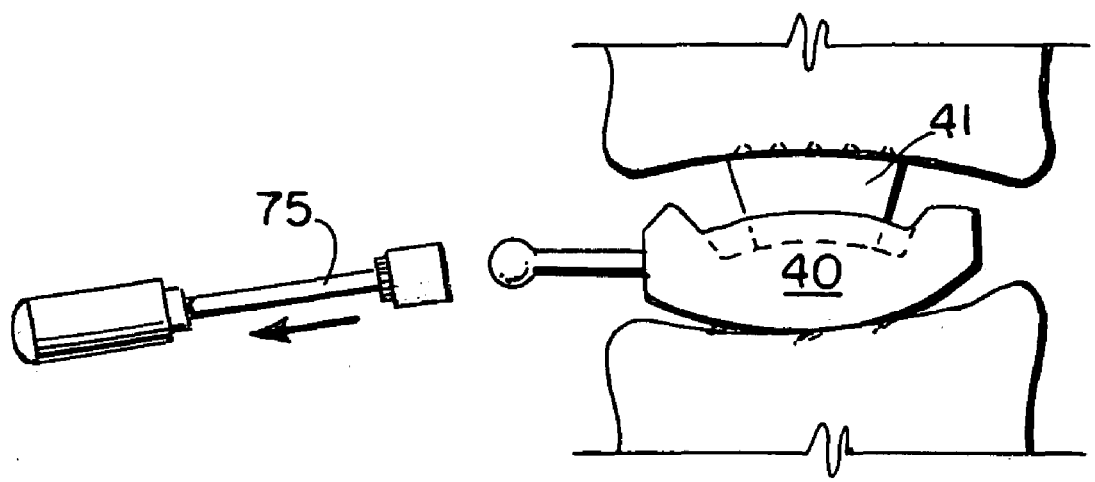
FIG. 18E shows side view of the assembled upper and lower implant of the tongue and groove embodiment in the disc space.
Figure 19:
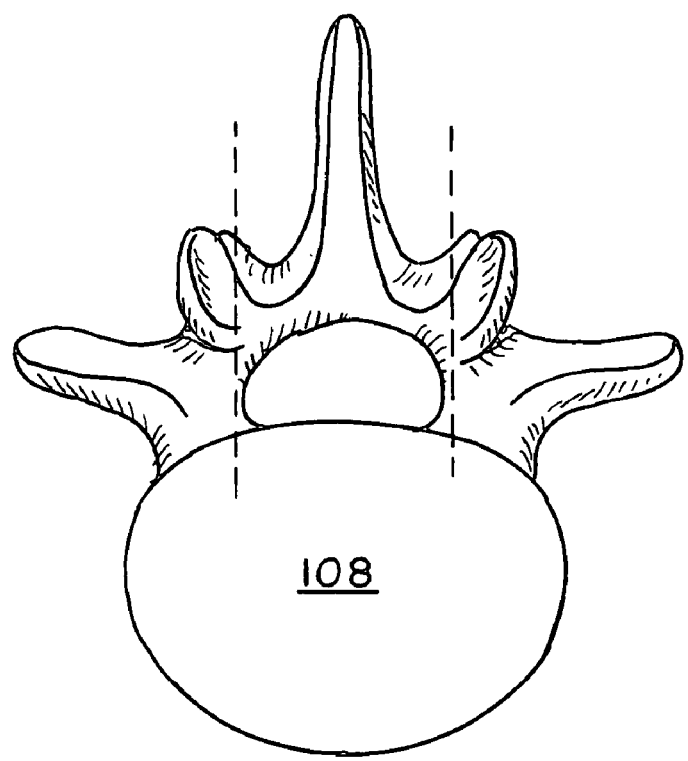
FIG. 19 shows the top cross-sectional view of spinal vertebra.

FIGS. 16 and 17 provide cross-section views of two embodiments of the upper implant with tongue 41. Specifically different configurations of the tongue 42 and complimentary groove 48 are shown. In one embodiment, a tight fit is shown in FIG. 16 between a rectangular tongue 42 and groove 48. This particular configuration would insure a more controlled movement permitting limited, if any, side to side movement with respect to the upper implant and lower implant. In FIG. 17, an alternative embodiment is shown where the groove 48 has a more rounded through shape which together with the curved posterior aspect of the tongue 42 of upper implant 41 permits a greater amount of freedom for side to side movement and rolling of the upper implant in relation to the lower implant. In these embodiments, the upper implant may not be permanently attached to the lower implant 22. Prevention of displacement or dislocation of the upper implant 41 with the lower implant 40 is insured by the tight fit and the contour of the disc space. Another embodiment is one in which the tongue and groove is "T-shaped" which would result in a more secure attachment of the upper implant and further reduce the already low probability of upper implant displacement or migration. The anchor rail design embodiment of the present invention absolutely prevents displacement or migration of the upper implant, since in that embodiment the upper implant is confined to a track defined by the post or guide rail and the central channel.

FIGS. 18A-18E show a multi-step process is illustrated for the sequential assembly of the two separate components of the tongue and groove design embodiment of the implant performed within the disc space. Alternatively, this assembly may be completed outside of the disc space, and the two components inserted simultaneously after the dimensions of the disc space can be determined such as by progressive trial implants. The separate component design of this embodiment allows for implantation of a device of appropriate size, so that the device closely approximates and tightly binds with the inner surfaces of the endplates of the upper and lower vertebra on either side of the disc space.

The body of the lower implant should fit in a typical disc space and can be approximately 2.5 cm in length and the upper implant can be approximately 1 cm to 1.5 cm in length with a total height of the assembled implant at 9 mm to 14 mm. The anchor shaft's length is approximately 15-20 mm and the width of the implant is approximately 10 mm or any workable length and width less than the patient's disc space. It is anticipated that the main variability in the assembly will involve selection of upper implants 41 of varying heights within the parameters of the size of the disc space. In this fashion, an upper implant of appropriate size can be chosen to insure a tight fit within the disc space resulting in optimum binding of the invention with the endplates of both of the vertebrae. For sequential insertion of the slot design embodiment of the present invention it is advantageous to place the upper implant 41 first, and the lower implant 40 next. The upper implant can be inserted together with the lower implant or separately. In any event it is important to maintain the orientation of the upper implant in a neutral location during placement of the lower implant. This proper placement can be insured by a holder/inserter tool 55, with side arms that can securely grasp the upper implant 41. As shown in FIGS. 18 A-B, the lower implant 40 is attached to an implant tool 75 and inserted into the disc space and tongue and groove joint is engaged. Once assembly is complete, the holder/inserter tool and implant tool are withdrawn.

Figure 20:
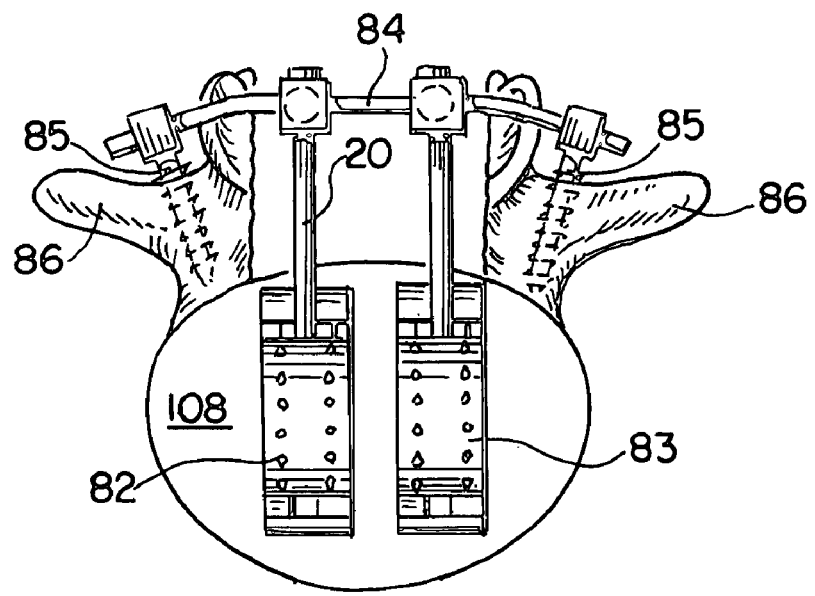
FIG. 20 shows the top cross section view of a pair of assembled implants in the vertebra's disc space.
Figure 21:
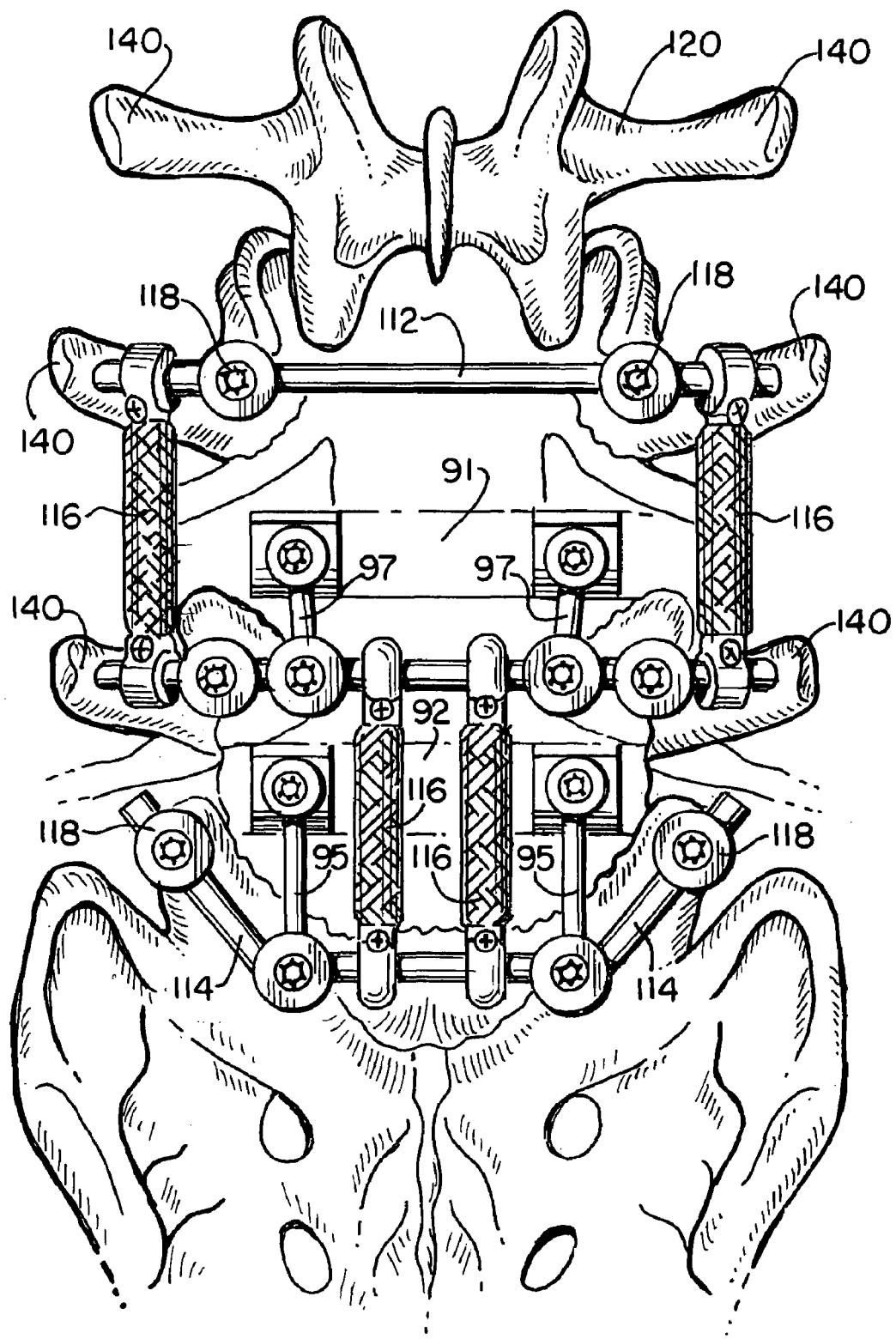
FIG. 21 shows a posterior view of the lower spine with a number of implants attached to a dynamic spinal stabilization system.

In FIGS. 20 and 21, a pair of assembled implants 82 and 83 are shown within the disc space and affixed to a transverse rod 84 and the transverse rod 84 is secured to by pedicle screws 85 to the vertebra 86. The rods should be sized to fit within the patient's transverse processes 140 with approximately 5-6 cm in length with width sufficient for attachment by pedicle screws.

Figure 22:
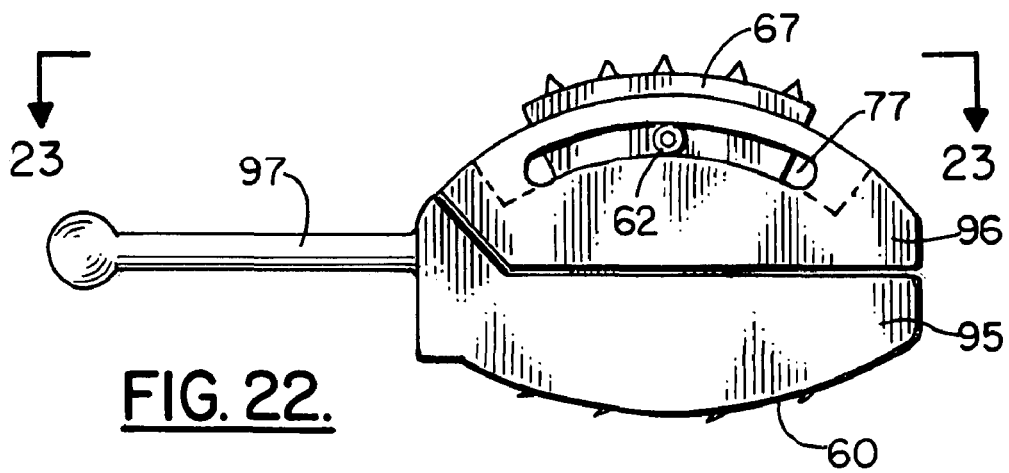
FIG. 22 shows a side view of the rotational post implant.
Figure 23:
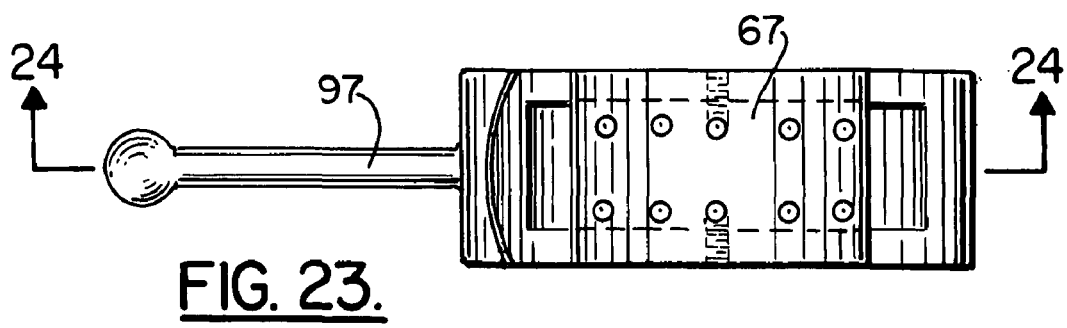
FIG. 23 shows a top view of the rotational post implant.
Figure 24:
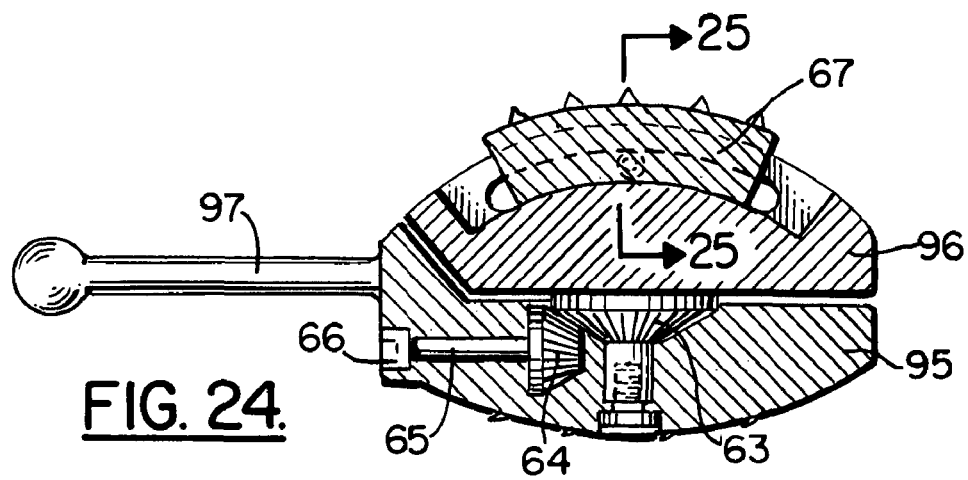
FIG. 24 shows a cross section view of the rotational post implant.
Figure 25:
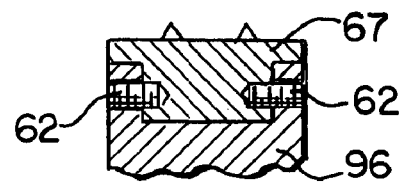
FIG. 25 shows a cross section of the upper implant of the rotational post implant along the lines of 25-25 of FIG. 24.
Figure 26:
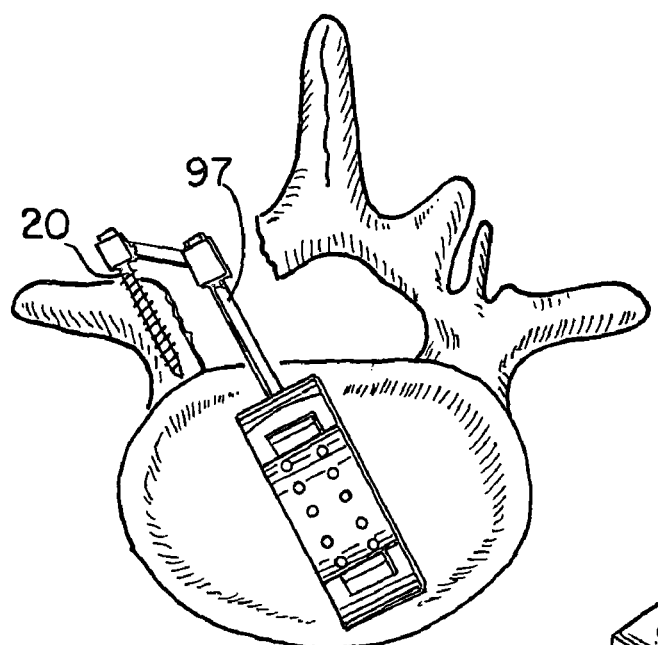
FIG. 26 shows a top view of the rotational post implant in the disc space.
Figure 27:
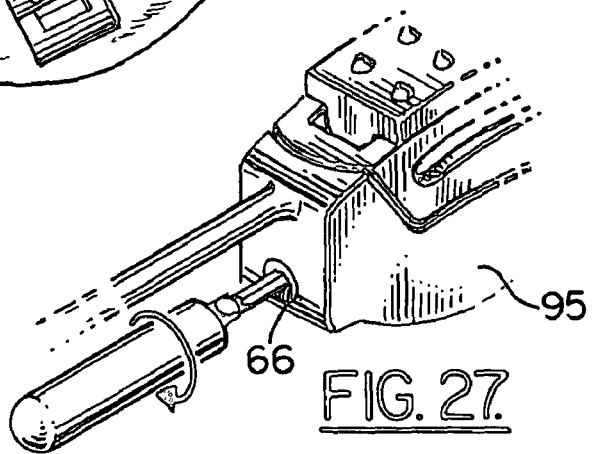
FIG. 27 shows a perspective view of the engagement of the gear mechanism.
Figure 28:
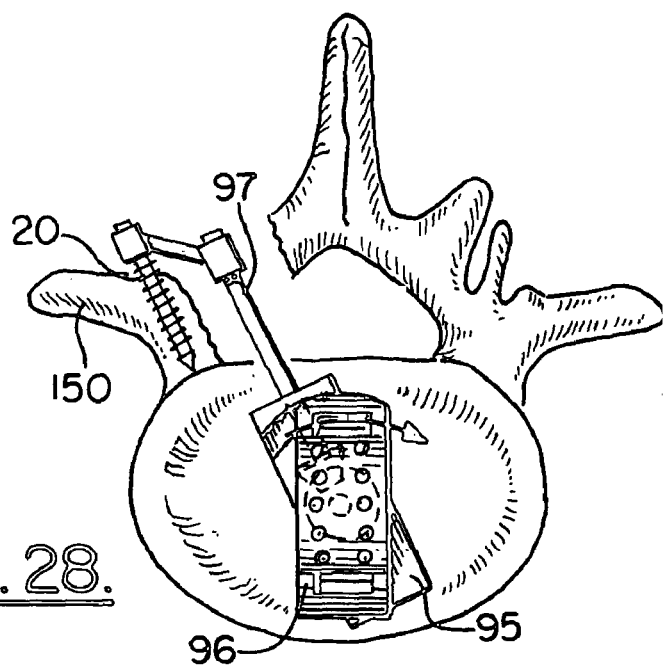
FIG. 28 shows a top view of the rotational post implant in the disc space.

Another embodiment of the implant according to the invention is disclosed in FIGS. 22, 23 and 24. This embodiment is referred to as the rotational post design. The lower implant has a lower section 95 that includes the anchoring shaft 97 and main body 60 in which is found the turnable axle 65 terminating in a small gear 64 and an upper section 96. The upper section 96 of this embodiment is comprised of the larger rotating gear and axle 63. The upper implant 67 can slide along a tongue 62 of the upper implant within grooves 77 in the upper section 96 of the lower implant. Different upper sections and upper implants 67 of varying heights would enable selection of a size compatible with the dimensions of the disc space. The implants are preassembled in this particular embodiment and can be inserted as a unit, after the disc space has been measured and prepared with a series of known temporary trial inserts. During the insertion process, the assembly can be secured with a holder/inserter tool, which can insure a correct neutral position of the upper implant 67 on the post 62. Once the implant is placed, the holder/inserter is removed and withdrawn. The head 30 of the anchoring shaft 20 is connected either directly or indirectly to a pedicle screw or stabilization device such as transverse rods 84 and dynamic stabilization rods that is placed independently in the pedicle of the lower vertebra. After placement in the disc space, the upper section is rotated with respect to the lower section as shown in FIGS. 27 and 28. The rotation is accomplished by turning the axle 65 until the lower implant is parallel and coplanar with the sagittal plane of the disc space and the adjoining vertebra. Correct orientation can be documented using X-ray fluoroscopy. When rotation is complete the orientation is secured by means of a locking screw 66. The anchor shaft 97 is attached to the pedicle 150 of the spine by pedicle screw 20. FIG. 28 shows implantation after removal of one facet of the spine. In this fashion flexion and extension of the spine in the sagittal plane is permitted. Similar to the tongue and groove embodiment, the configuration of the post and the central channel through the upper implant can be designed to allow for some side to side and rotational movement of the upper vertebra with respect to the lower vertebra. Should removal of the implant be required in the future, the implant according to the present invention advantageously allows for derotation of the upper implant. This is accomplished by removal of the locking screw 66 and turning the axle 65 connected to the small gear 64 in the direction opposite to that used during implantation. After the orientation of the upper section is realigned with the lower section, extraction of the entire assembly is facilitated.

The rotational post design is preferably larger in overall dimensions than either the simple post design or the slot design embodiments. Additionally as shown in FIG. 28, the rotational post design is preferably for solo use in the disc space. In contrast the simple post design or the slot design is preferably for paired usage at each disc space as shown in FIG. 10. In all cases, however, the embodiments share the common design characteristic of stable positioning of the implant as a result of the connection between the anchoring shaft 20 and a pedicle screw 80. In the simple cross-sectional view of FIG. 28 a direct connection to the pedicle 81 is illustrated.

A representation of one potential method of indirect attachment and incorporation of an embodiment of the dynamic spinal stabilization device is shown in FIG. 21. Stabilization of both the L4-5 and the L5-S1 disc spaces is revealed. In this non limiting example, paired simple post or slot devices are utilized. FIG. 10 shows the lower lumbar spine having vertebra L-3 140, L-4 142, L-5 144 and the sacrum 146 with removal of the posterior elements.

As has been previously stated, these embodiments require a laminectomy and at least partial and usually total removal of the posterior vertebral elements as shown in FIGS. 10 and 11. For that reason, the devices according to the present invention should be utilized in conjunction with a posterior dynamic stabilization system. One embodiment of the dynamic spinal stabilization system can include various straight transverse members 112 and curved transverse members 114 attached to the spine 120 by pedicle screws 118 and the members attached to the anchor posts 97 of implants in the disc spaces with flexible rods 116 attached to the members 112 and 114 providing dynamic stabilization to the spine as shown in FIG. 21.

The paired implants according to the present invention are seen in the L4-5 disc space 91 and the L5-S1 disc space 92. The connection between the anchoring shaft and the transverse members and to the flexible rods may be achieved through a variety of known means. As previously stated, it is anticipated that the top of the anchoring shaft 97 will be fitted with a multi-axial head similar to those found on commercially available polyaxial pedicle screws.

Figure 32:
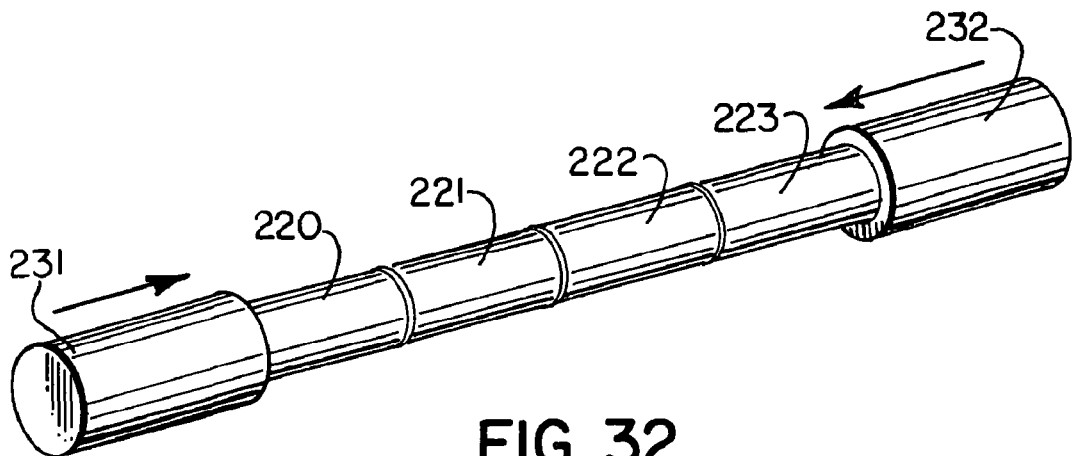
FIG. 32 shows a side perspective view of the dynamic spinal stabilization device's inner or first layer in the neutral or resting state at minimum length.

An embodiment of the dynamic spinal stabilization device is compromised of three layers or tiers arranged concentrically and nested one within the other culminating in a general rod-like shape. Cross-section of the dynamic spinal stabilization device would reveal the tiers to be arranged like the layers of an onion or the rings in a tree. The inner most or first layer is shown in FIGS. 29 and 32, in which the individual bullet elements, 220, 221, 222, 223 have the form and shape shown in FIG. 35. In FIGS. 29 and 32 are shown four individual bullet elements, 220, 221, 222, 223 but a greater or smaller number may be employed without departing from the spirit and scope of the invention. The bullets are 3-5 mm in length forming a rod that can be 12-30 mm in length depending upon the number of bullets. As those skilled in the art can readily appreciate, it is desirable to be able to select from an assortment of rod-like shapes of differing lengths based upon the specific anatomic requirements of the surgical implantation. These bullet elements may be made from any suitable material, including but not limited to ultra high molecular weight polyethylene UHMWPE, polyetheretherketone PEEK, or a metal such as a titanium alloy coated with a material with a low coefficient of friction such as UHMWPE.

Figure 33:
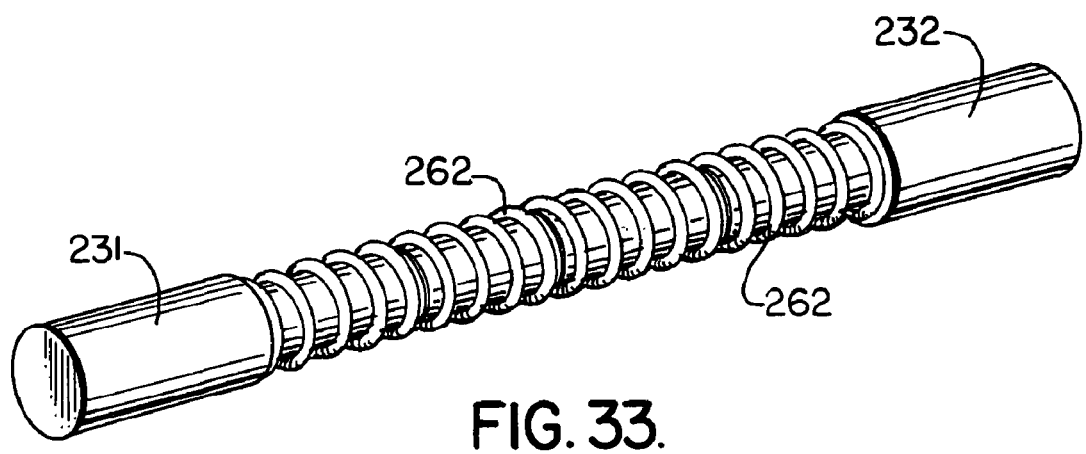
FIG. 33 shows a side perspective view of the dynamic spinal stabilization device's middle or second layer in the neutral or resting state at minimum length.

Each of these bullet elements has an upper side 227 as well as a lower side 228 that allows for an interconnected stack series of bullets, 220, 221, 222 and 223 with the upper side 227 fitted into the adjacent bullet's lower side 229. Other embodiments can confer different flexibility characteristics on the dynamic spinal stabilization device, and would not depart from the spirit and scope of the invention. Additionally at the bottom end of the stacked bullets 220, 221, 222, 223 is a bottom attachment element 231, and at the top end of the stacked bullets is a top attachment element 232. The bottom attachment element 231 has an upper side 218 for insertion into a compatible lower side 229 of bullet 220. The top attachment 232 has a lower side 217 forming a cavity sized to receive the upper side 229 of the adjacent bullet 223. The individual components of the inner tier, which include the two attachment elements, 231 and 232 and the intervening bullet elements 220, 221, 222, and 223 interconnect with one another when the stack of bullets are resting at minimum length without elongation shown in FIGS. 32, 33 and 34. Because of this interaction or interconnection of the upper 227 and lower sides 229, the stacked bullets 220, 221, 222, and 223 with the top attachment 232 and bottom attachment 231 become generally rigid, and little to no flexibility shown in FIGS. 32, 33, 34, 38, 40 and 45. However, when the stacked bullets 220, 221, 222, and 223 are separated by elongation as a result of applied longitudinal tension, the individual bullets 220, 221, 222, and 223 of the inner tier no longer fully interconnect with each other. This elongation of the bullets 220, 221, 222, and 223 is shown in FIGS. 29, 30, 31, 39, 41, 42 and 45. As a result, angular movement can occur between the individual bullets 220, 221, 222, and 223 and attachment elements 231, 232 and some degree of flexibility is imparted to the dynamic spinal stabilization device as shown in FIGS. 39, 41 and 45. The attachment ends are sized to be compatible with the attachment means such as sized to fit a pedicle screw. The diameter can be ¼ inch or ⁵⁄₁₆ inch. The bullets can be alternatively flexibly attached or connected together by tethers attaching adjacent bullets. A tether 215 can allow flexible connection of the bullets and provides for a terminal elongation of the bullets. The tether 215 should be made of suitable durable material for implantation such as a braided titanium cord. Alternatively, the bullets can be flexibly attached by other material such as strips of fabric, metal or plastic attaching the bullets to each other in a flexible manner limiting complete separation of the bullet elements.

Figure 35:
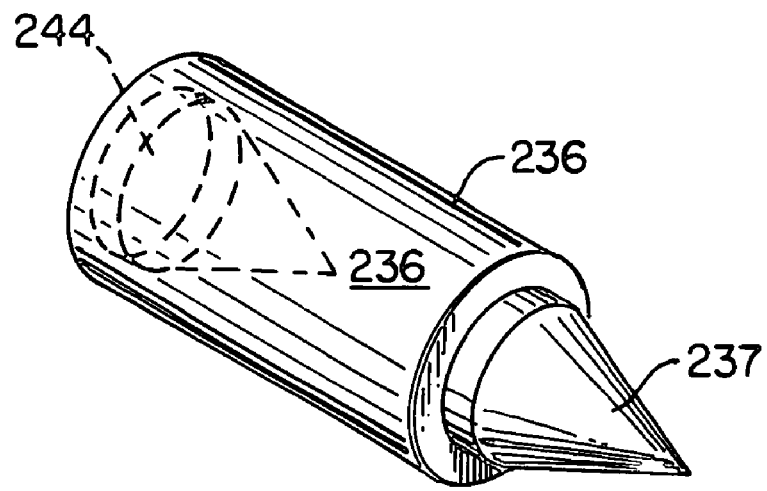
FIG. 35 shows a side perspective view of one embodiment of an individual bullet element from the inner or first layer of the dynamic spinal stabilization device, termed the cone shaped design.
Figure 36:
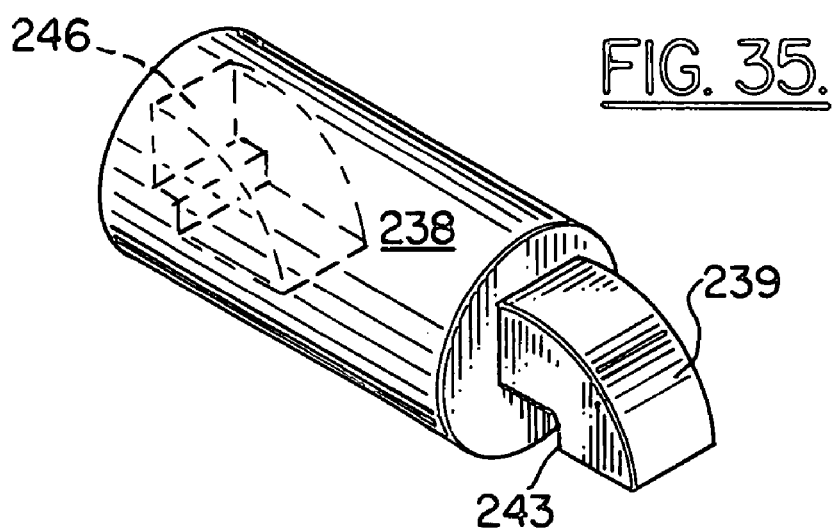
FIG. 36 shows a side perspective view of another embodiment of an individual bullet element from the inner or first layer of the dynamic spinal stabilization device, termed the curved hook design.
Figure 37:
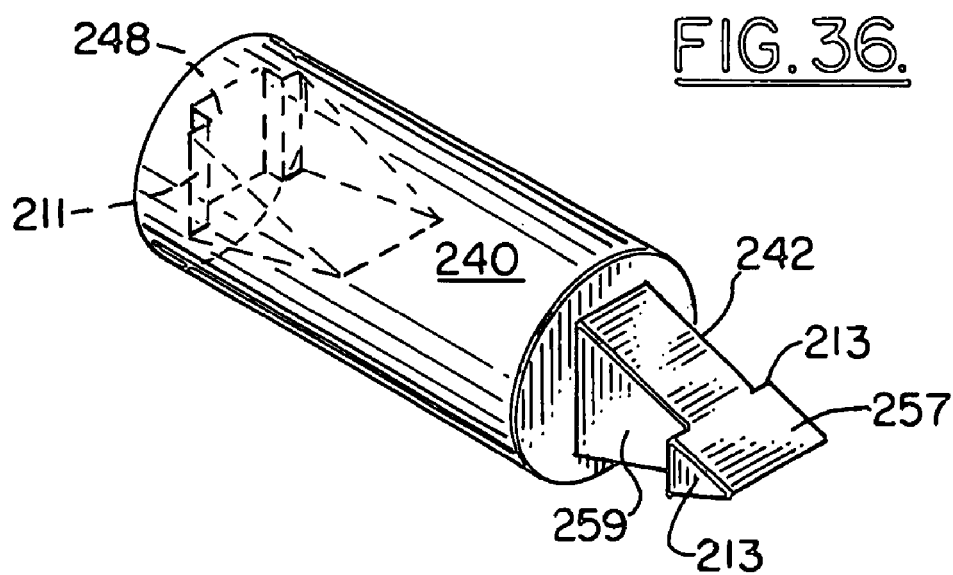
FIG. 37 shows a side perspective view of another embodiment of an individual bullet element from the inner or first layer of the dynamic spinal stabilization device, termed the flat arrow design.

The shape and design of the individual bullets influence, direct and dictate the amount and direction of flexibility permitted after the initial elongation of the invention. In particular, the shape and design of the upper side and lower side are responsible for this property of the invention. Three exemplary but non-limiting embodiments of the bullets are presented in FIGS. 35, 36 and 37. In FIG. 35, a cone-like design for the upper side 237 of bullet 236. In FIG. 36, the bullet 238, has an upper side forming a curved hook or quarter cylinder configuration 239 with a bottom side ledge 243. In FIG. 37, the bullet 240 has "flat arrow" design for the upper side 242. Designs or configurations of the upper side of the bullets or the shape of the bullets other than those shown would not depart from the spirit or scope of the invention. Each bullet has a correspondingly designed lower side 244, 246 and 248 which permits insertion and interlocking with complementary upper side 237, 239 and 242 respectively of an adjacent bullet.

The flexibility permitted by the cone design is shown in FIG. 39. When in the resting state at minimum length, the individual bullets of the inner tier are interlocked and the inner tier is generally rigid when the collar 250A at the base of the cone is fully inserted in the adjacent bullet lower side cavity 244.

The stacked series of bullets and attachment elements can be secured to the patient's spine by attachment means such as pedicle screws that are affixed to the attachment elements, and when flexion of the spine is attempted, the distance between the pedicle screw heads is increased. This flexion produces longitudinal tension between the attachment elements resulting in an unlocking and separation of the bullet elements. Increased flexion results in a widening gap between the upper ends and lower ends of neighboring bullet elements. As can be seen in FIGS. 39, 41 and 45, this permits angular flexibility between the bullet elements 220, 221, 222, and 223 resulting in bending of the bullets with respect to each other. In an embodiment with the cone shaped design 237 being symmetrical, bending of the bullets 220, 221, 222, and 223 in all planes is equally permitted. The bullets 220, 221, 222, and 223 in the resting state resist buckling with reverse bending of the spine, called extension. In this manner, bending of the bullets and therefore of the invention as a whole is allowed with spinal flexion, but resisted with spinal extension.

Limited flexibility permitted by the curved hook design 239 is shown in FIGS. 39, 40 and 41. When in the resting state at minimum length, the individual bullets 220, 221, 222, and 223 are stacked and interlocked and the inner tier stack of bullets are generally rigid. When flexion of the spine is attempted resulting in movement of the two vertebra, the distance between the pedicle screw heads attached to the bottom attachment element 231 and the top attachment element 232 is increased. This produces longitudinal tension between the top attachment element 232 and bottom attachment element 231 resulting in a separation of the curved hook 239 and the lower side 246 of the bullet elements 220, 221, 222, and 223. Further elongation of the stacked bullets 220, 221, 222, and 223 results in a widening gap between the upper and lower components of neighboring bullet elements. As can be seen in FIGS. 41 and 42 this permits angular flexibility between the bullet elements resulting in bending of the inner tier of stacked bullets. The shape, size and design of the upper side 239 and lower side 246 generally restricts motion and limits bending of the stacked bullets except in a plane parallel to its curved surface of upper side of the curved hook 239 and in a direction opposite to its curved surface. In particular a downward bending may be permitted as in FIG. 41, which corresponds to spinal flexion. Upward or reverse bending is resisted even with elongation of the invention as shown in FIG. 42. Therefore spinal extension is restricted. Side to side or lateral bending of the stacked curved hook bullets is restricted. This type of movement would be permitted after elongation with the cone design 237. However, the curved hook design restricts side to side or lateral bending because of the flat shape of the sides of the upper 239 and lower 230 components of the curved hook bullet element. Flexibility and bending is possible only in a plane parallel to the curved surface and in a direction opposite to that curved surface.

Another aspect of the curved hook design is the downward projecting ledge 243 and its corresponding lower edge 247 of the opening of the lower side 246 of the adjacent bullet to prevent the hook from completely separating from the cavity of the lower side 246. These two features functioning together encourage an even and constant spacing between the individual bullet elements as the invention is elongated and the distance between the two end attachment elements is increased. Otherwise, it is possible that the distance between bullet elements could vary too much, resulting in uneven and patchy flexibility of the invention. Several bullets might remain stuck together and interlocked, with all of the separation occurring between only a few of the bullet elements. The hook design 239 advantageously encourages a more even spatial distribution of the bullet elements as the dynamic spinal stabilization device is lengthened.

An alternative embodiment utilizes a central guide wire 252 of length sized to pass through all bullets disposed through the individual bullet elements within a central passage or canal 55, placed down the longitudinal axis of each bullet 256 in order to achieve a more even spatial distribution. The central guide wire 252 can be permanently or temporarily placed in this central passage 255 through each bullet element as well as through each attachment elements 231 and 232 thereby conferring additional rigidity on the assembly. The guide wire 252 can be attached to the bullets by threaded screw attachment or other attachment means such as clasp, hook or locking nut.

The guide wire 252 can rigid or flexible and is made of a suitable material for implantation such as titanium alloy. The guide wire can have a shape memory quality. The length is governed by the size and number of bullets. The guide wire 252 can have some rigidity to impart rigidity and flexibility to the bullets depending upon the amount of flexibility or rigidity of the wire.

Another bullet 240 embodiment has a flat arrow upper side 242 as shown in FIG. 37 having two opposite sides 257 tapering to a narrower distal end and two remaining sides 259 are flat and generally parallel. This shape of the upper side 242 permits the relatively free movement in up and down bending similar to the cone shape along the tapered sides, but tends to restrict side to side bending along the flat sides in a manner analogous to the curved hook design 239. Although upward bending is possible with coincident elongation, no upward; bending would be permitted with compression of the invention. That is a result of the interlocking of the individual bullet elements which resist bending in the compressed state. Extension of the spine results in and is possible only with a decrease in the distance between the upper posterior aspects, also called heads, of the pedicle screws 216. This would result in compression of dynamic spinal stabilization device, since the dynamic spinal stabilization device is attached at each end either directly to pedicle screws 216 or indirectly to transverse rods 254 which themselves are attached to pedicle screws 216. Since spinal extension would occur only with compression of dynamic spinal stabilization device, any extension resulting in compression of the dynamic spinal stabilization device past its fully compressed state would be resisted. The dynamic spinal stabilization device according to the present invention therefore has an important structural advantage over many other dynamic stabilization devices. Due to the interlocking of the bullet points at the point of minimum length, buckling would be resisted.

Many other design variations and embodiments are possible without deviating from the spirit and scope of the invention. For example, a contoured design of the bullets 256 is presented in FIGS. 44 and 45. Each individual bullet 256 is curved so that the stacked bullets have a curved rodlike shape in the resting or neutral and nonelongated state. Therefore the stack of bullets in this embodiment can have a shape which can correspond to the normal curvature of the lumbar spine, which is termed lumbar lordosis. Therefore the bullets 256A, 256B, 256C, and 256D revealed in FIGS. 44 and 45 are described as the "curved hook" design. This particular design has the same bending and movement characteristics as the curved hook design. In particular, flexibility in one plane is advantageously permitted. This lordotic shape and temporarily increased rigidity would permit percutaneous or open minimally invasive surgical implantation. Once the dynamic spinal stabilization device is placed and secured in the pedical screw heads, the guide wire can be withdrawn.

Additional design embodiments for the upper and lower components of the bullet elements are possible without departing from the spirit or scope of the invention. For example, an upper side shaped like a cone with flat sides would restrict side to side bending. Upward bending would be possible, but with spinal extension the pedicle screw heads move closer together. This movement compresses the invention, causing the individual bullet elements to interlock and conferring rigidity on the invention. Therefore spinal extension is resisted and buckling of the invention is prevented. Spinal flexion would be allowed in association with elongation of the invention. The distal end of the arrow is wider than the middle forming winged edges 213 and a corresponding lower surface of an adjacent bullet can be designed which would allow combined smooth functioning of the assembly. These winged edges 213 contact a ridge 211 in the cavity of the bottom side of the adjacent bullet preventing the arrow from separating out of the cavity.

The dynamic spinal stabilization device can have a middle or intermediate layer or tier. This tier is composed of an extension spring 262, shown in FIGS. 30 and 33. This extension spring 262 can be manufactured from any suitable shape memory material, including but not limited to a titanium alloy of size and length to encase the bullets. This extension spring 262 is designed to resist elongation, and has a resting or neutral length that results in the individual bullet elements 220, 221, 222, and 223 closely approximated with firm interlocking of each upper side with its corresponding lower side. In this manner, rigidity is conferred on the invention in the neutral or resting length. Springs are inherently flexible, and will reflect the amount and degree of flexibility allowed by the stacked bullets 220, 221, 222, and 223 which is composed of the individual bullet elements and the two end attachment elements. The only resistance provided by the spring 262 is resistance to elongation. Specifically the spring 262 has no resistance to bending. However, when the spring 262 encases the individual bullet elements in which the outer diameter of the bullets closely approximates the inner diameter of the spring 262, the spring 262 takes on the flexibility and bending characteristics of the bullet elements 220, 221, 222, and 223 acting in concert. Specifically resistance to buckling is a characteristic of the present invention. Furthermore, the amount and direction of flexibility of the spring 262 will be determined by the design of the bullet elements comprising the inner tier or first layer of the invention. The composition and physical properties of the spring for resistance to elongation can be chosen to achieve the desired resistance to elongation. The spring can be attached to the bullets at the top and bottom of the stack.

Figure 34:
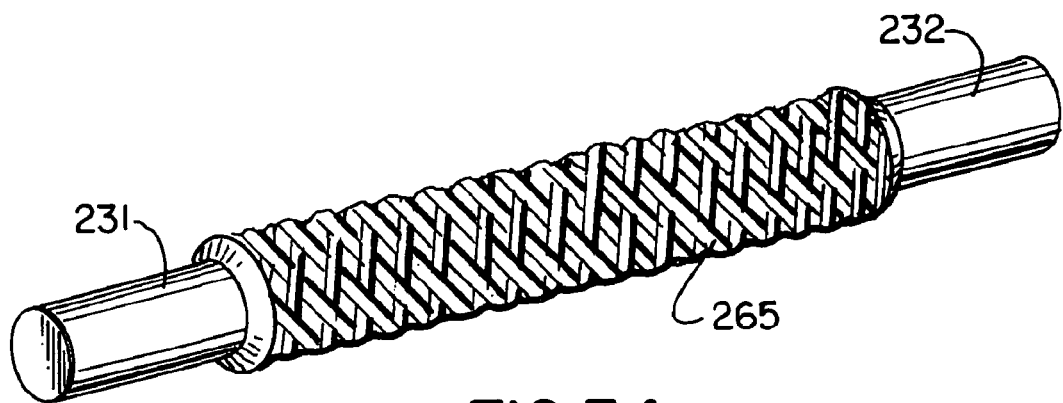
FIG. 34 shows a side perspective view of the dynamic spinal stabilization device's outer or third layer in the neutral or resting state at minimum length.

The device according to another embodiment can have a third or outer layer or tier. This layer is composed of a sleeve of suitable material woven 265 in the form of a Chinese finger trap. The material can be fabric, metal, plastic or other suitable material. In FIG. 34, the woven material layer 265 is shown in the resting or neutral state of the invention, where length is the shortest. The sleeve of woven material 265 can be seen as loose and the outer layer is somewhat bulging. In FIG. 31 the sleeve of woven material 265 is seen with a tight weave pattern and the diameter has constricted and tightened to closely approximate the outer diameter of the spring 262. This tightening and constriction imparts stiffness and rigidity when the invention is elongated. This phenomenon has been described in devices designed as compression bandages, finger traction devices, and patient restraint devices as disclosed in U.S. Pat. Nos. 1,268,932; 2,783,758; 3,872,861; 4,728,329; 4,917,700; 5,027,802; 5,074,291; 5,451,203; and 5,649,541. The purpose of the third tier of the sleeve of woven material 265 is to provide an absolute limit to the amount of elongation of the invention. This imparts a safety stop and reduces progressive wear of the spring 262 since stretching beyond a certain point is prevented. At the same time that the third tier elongates it constricts and reduces its diameter. This property is preferably conferred on the woven material 265 by the weave pattern in the form of a Chinese finger trap. This constriction of the woven material 265 tightly around the outside of the spring 262 provides a degree of stiffness and rigidity to the invention. Therefore with elongation of the invention as some of the rigidity is lost by distraction and separation of the individual bullet elements 220, 221, 222, and 223, a degree of rigidity is restored and reacquired by the constricting action of the woven material 265. The sleeve can be attached to the bullets, the spring or both.

In this preferred embodiment, the dynamic spinal stabilization device according to the invention has three layers or tiers, arranged concentrically one within the other with the stacked bullets 220, 221, 222, and 223 making up the first layer and the spring 262 making up the second layer and the woven material 265 making up the third layer. Other embodiments and various arrangements of the layers would not depart from spirit and scope of the invention.

Figure 31A:
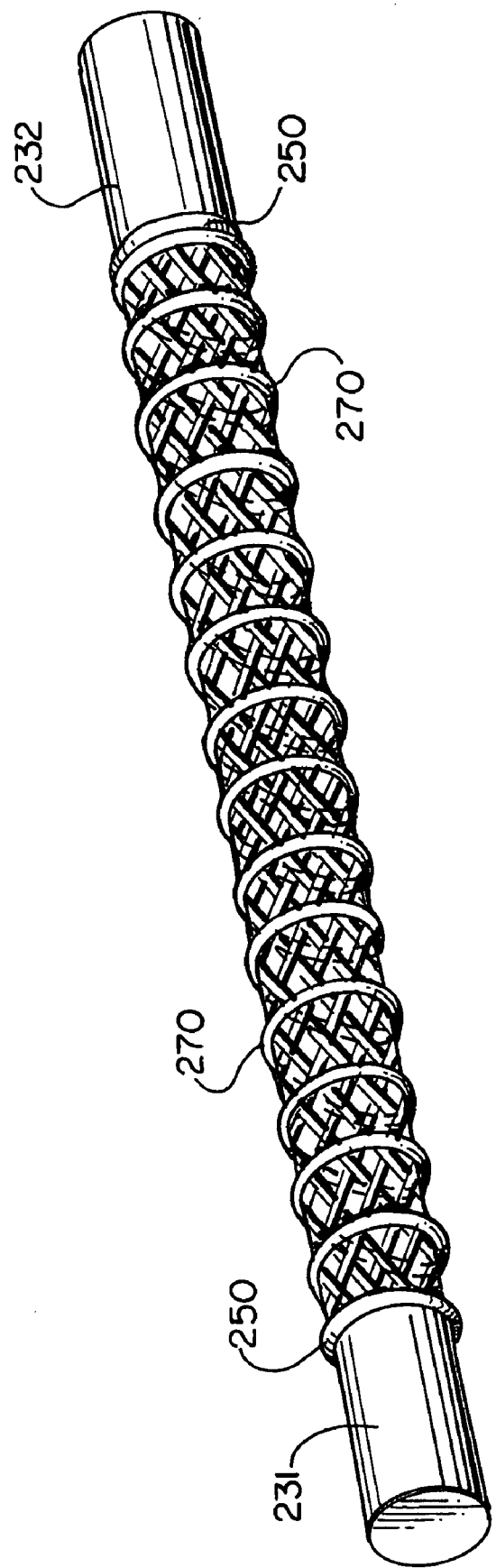
FIG. 31A shows a side perspective view of the dynamic spinal stabilization device's fourth layer in a state of elongation at greater than maximum length.

A fourth layer could be applied consisting of a compression spring around the woven fabric 265 as shown in FIG. 31A. A balance in the resting state could be achieved between the extension spring 262 in the second layer with the compression spring 270 of the fourth layer. The extension spring 262 can be preloaded with a small amount of elongation, maintained in the resting state by the compression spring 270. In this manner some amount of flexibility would be permitted in the resting state due to some degree of separation between the individual elements of the first or inner most tier. With extension or backward bending of the patient's spine, the invention would be compressed between the heads of the pedicle screws 16 to which it is attached either directly or indirectly. With compression and shortening of the invention the individual bullet elements 220, 221, 222, and 223 interlock with one another, and rigidity and resistance to buckling is provided. The fourth layer spring can be attached to the sleeve, second tier spring, the bullets or any combination.

The dimensions of the dynamic spinal stabilization device as shown in the figures are non limiting embodiments. Specifically, a typical dimension is that of the terminal portions of the attachment elements 231 and 232, which preferably correspond in diameter to commonly used rigid rods in order to allow utilization with readily available and commonly used pedicle screw systems. However, the inner aspect of each attachment element 231 and 232 will be significantly larger in diameter due to the presence of the attachment element collar 250 shown in FIG. 31. The design, construction, and dimensions of the attachment element collar 250 will allow for the unified grouping of all three layers or tiers of the invention: the first tier comprised of the individual bullet elements 220, 221, 222, and 223 and bounded by the inner or medial aspect of each attachment element; the second tier comprised of the extension spring 262; the third tier comprised of the woven material 265 in the pattern of a Chinese finger trap; and optionally a fourth layer comprised of a compression spring 270 as shown in FIG. 3A.

Figure 47:
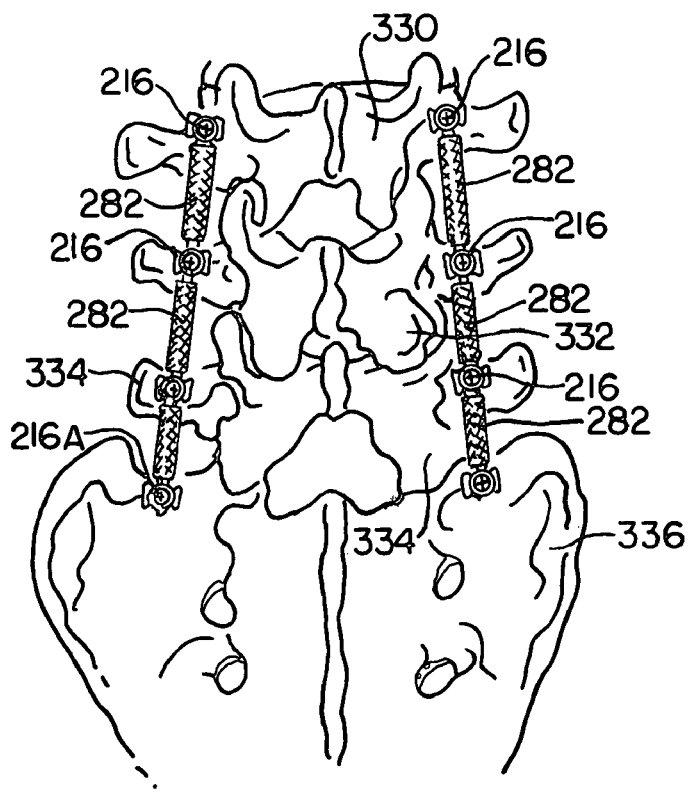
FIG. 47 shows a perspective view of multiple devices connected to the spine via pedicle screws.
Figure 48:
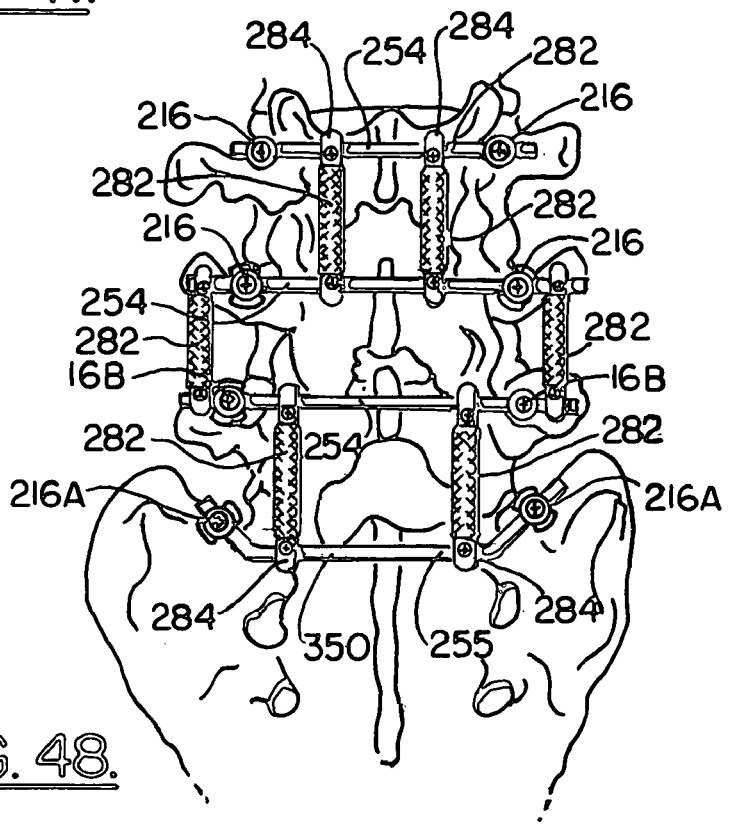
FIG. 48 shows a perspective view of an arrangement of multiple dynamic spinal stabilization devices connected to the spine indirectly via pedicle screws using intermediary transverse rods.
Figure 52:
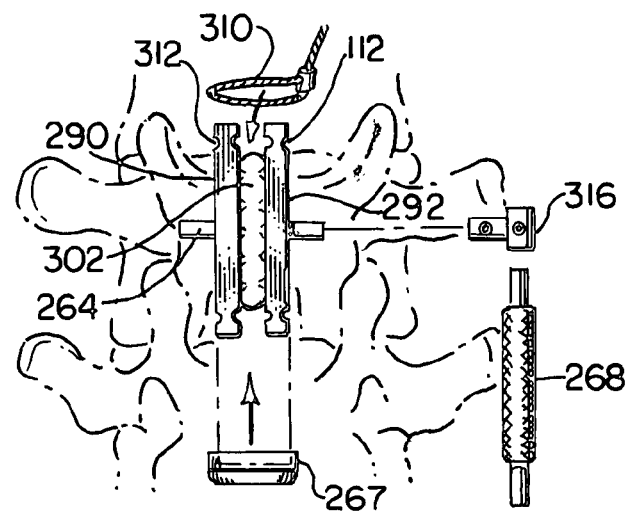
FIG. 52 shows a perspective view of the attachment of the paired plates and dynamic spinal stabilization device to a spinous process.
Figure 53:
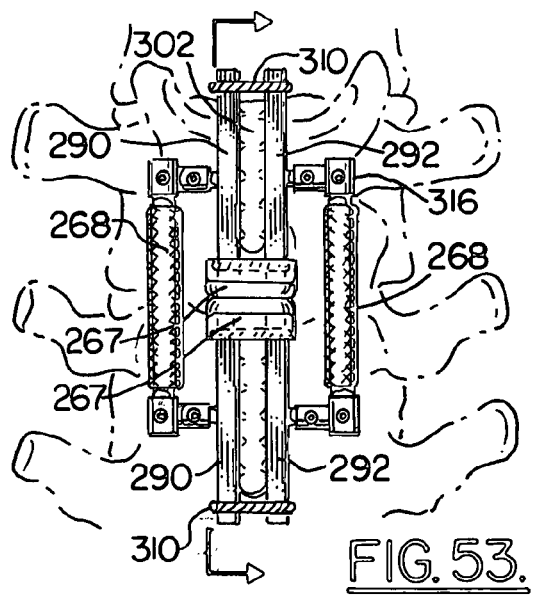
FIG. 53 shows a perspective view of paired plates and paired dynamic spinal stabilization devices linking two contiguous spinous processes.
Figure 54:
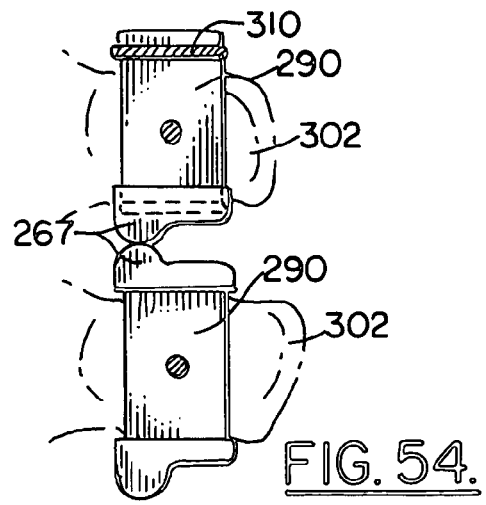
FIG. 54 shows a side view of the dynamic spinal stabilization device attached to two contiguous spinous processes.
Figure 55:
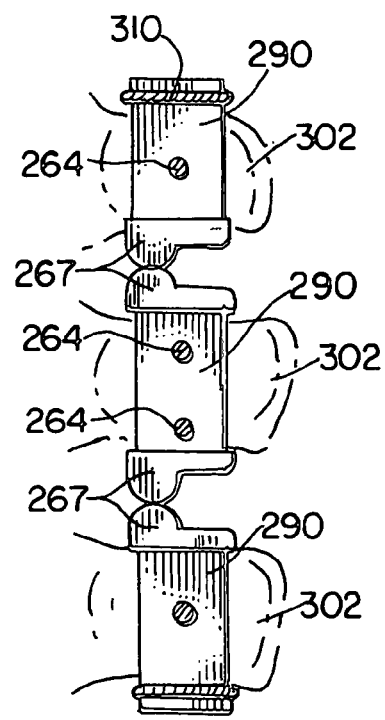
FIG. 55 shows a side view of the dynamic spinal stabilization device attached to three contiguous spinous processes.

Several methods of surgical implantation of the present invention are disclosed in FIGS. 47, 48 and 49. For illustrative purposes, only methods for providing dynamic stabilization are shown for three motion segments involving four vertebral bodies L-3, L-4, L-5, S-1 shown as 330, 332, 334, 336 in FIG. 47. A greater or lesser number of motion segments of vertebra can be stabilized. Pedicle screw implants are widely utilized by those skilled in the art, and several options are commercially available, such as SCIENT'X and Medtronic (www.medtronic.com). This preferred embodiment contemplates either direct or indirect attachment to these pedicle screws 216. FIG. 47 reveals the technique of direct attachment to polyaxial pedicle screws 216.

A multisegment dynamic spinal stabilization device constructed in series with multiple attachment elements is shown in FIG. 48. However, as those skilled in the art can readily appreciate, it would be difficult to estimate in advance the spacing required for the location of the various attachment elements to enable fixation direct within the polyaxial pedicle screw heads, unless only one motion segment was being stabilized. In order to employ the direct method for more than two pedicle screws, an assortment of varying lengths and spacing of attachment elements would have to be available. In FIG. 47, as is obvious to those skilled in the art, the distance between the screw heads 216A in the L5 vertebral pedicle 334 and the screw head 16B of S1 vertebral pedicle 336 is always very short, sometimes less than 1 cm. In FIGS. 48 and 49 the contour of the transverse rod 314 allows greater distance between screws 216A and 216B.

FIGS. 48 and 49 show a manner and method of indirect attachment to pedicle screws employing intermediary transverse rods 254. A special type of contoured transverse rod 55 is attached between the S1 pedicle screws 251A and 251B. The concept of contoured transverse rod is very different from the idea presented in U.S. Pat. Pub. No. 2006/0084991, since in the present invention the contour increases rather than decreases the distance between the transverse rods. Furthermore the transverse rods 254 and 255 in the present invention do not articulate directly with one another, either by means of a coupling joint or with a central spacer. The transverse rods 254 and 255 utilized in the present invention are a standard type rod commonly utilized in commercially available fusion instrumentation systems such as pedicle screws and rod implants manufactured by SCIENT'X and/or Medtronic. The indirect method of use and implantation described herein for the present invention provides three advantages over the direct method as seen in FIG. 47. The individual dynamic spinal stabilization devices are utilized even when providing dynamic stabilization to multiple spinal motion segments. The transverse rods have the ability to increase the distance between the attachment points of the L5 and S1 vertebral bodies. This is accomplished by the contoured intermediary rod 255. This increased distance allows for implantation of a longer dynamic spinal stabilization device 282, with the result that the implanted invention has increased flexibility characteristics thereby improving the dynamic stabilization between the L5 and S1 vertebrae. The indirect method provides increased inherent stability of the entire construct as a result of the transverse rods 254 and 255 themselves, with the resultant load sharing between both pedicle screws 216 of each vertebra. A further benefit is the inherently greater stability to rotation provided by locating the dynamic spinal stabilization device 282 further from the midline of the vertebra.

The dynamic spinal stabilization device may be implanted utilizing either the direct or indirect method of attachment to pedicle screws 216. In either method implantation may occur with the flexible rod 282 in the resting state of minimum length, or implanted at a length that is intermediate between its minimum and maximum length. The most advantageous strategy would be employed on an individual basis and would be predicated on the position of the spinal bones at the moment of surgical implantation. For example if the patient is positioned on the operating table with the spine in full or nearly full extension, then obviously no additional extension would be desirable afterwards. In that circumstance the dynamic spinal stabilization device 282 would be implanted in its resting state of minimal length. On the other hand, if some additional spinal extension is judged to be desirable after surgery, than the dynamic spinal stabilization device can be implanted in an intermediate length. The amount and degree of allowable movement could be readily ascertained during the surgical procedure by varying the distance between the transverse rods 254 (for the indirect method) or between the pedicle screw heads 216 (for the direct method). An alternative to loading the preferred embodiment of the flexible rod 282 in some tension and partial elongation, another embodiment of the dynamic spinal stabilization device can be implanted. As mentioned earlier another embodiment is constructed with four rather than three tiers. The fourth or outer most tier in this embodiment is a compression spring 270. The characteristics of this spring 270 would be complimentary to the extension spring 262 located in the second tier. The result of the combined and balanced but opposing forces of these two springs is that the resting or neutral state of the device would be of an intermediate length, neither in complete compression nor in full elongation. This would enable some degree of spinal extension when the dynamic spinal stabilization device 282 was implanted in its neutral or resting state.

The connectors 284 utilized for the attachment at either end of the dynamic spinal stabilization device 282 to the transverse rods can be of various designs. One example of such a connector is disclosed by U.S. Pat. No. 5,474,551 and U.S. RE39,035 E.

A method and apparatus for attachment of the dynamic spinal stabilization device is presented in FIGS. 50 through 55. Paired plates 290 and 292 are attached to the spinous processes 302 of the vertebra instead of directly to pedicle screws or indirectly via transverse rods. The spinous process attachment device is composed of paired plates 290 and 292 as seen in FIGS. 50 and 291 and 292 as seen in FIG. 51. The bone of the spinous process 302 is sandwiched between the plates 290 and 292, which are affixed to the spinous process by an attachment means such as a clasp, hook, interlocking elements or by a looped cable 310 such as a braided titanium cable. The inner surfaces of the plates can be roughened or have spike like projections 260 to grip and/or attach to the surface of the bone. If a cable is used to secure the plates, notches 312 can be fashioned in the plates 290, 292 to allow for secure seating of the braided titanium cable 310. The cables are commercially available and are commonly in use by those skilled in the art. The plates 290, 292 have short side projecting rods 264 or other attachment means to connect to the dynamic spinal stabilization device. FIG. 51 shows a variation of the plate design that is constructed with two pair of side projecting rods 223, which is also demonstrated in the center plate of FIG. 55. FIG. 51 also reveals another design variation which is the ability to pass the braided titanium cable through holes 314 within the plates, and if desired, though the substance of the bony spinous process 302 itself rather than on either side of it, in order to tighten and bind the plates tightly to the bony surface. The plates can be constructed of durable material suitable for implantation such as titanium. The paired plates 290, 292 are sized and shaped to fit on the spinous process. The spinous process typically has a thickness of 8 mm and a height of 25 mm. The plates can be sized 25-50 mm with a width of 3-6 mm.

The dynamic spinal stabilization device 268 is attached to the side projecting rods 264 using attachment means 316. Bumper or spacer elements 267 are attached to and positioned at the bottom or top of the paired plates between adjacent spinous processes. The bumper or spacer elements can be fabricated from a material having a low coefficient of friction such as UHMWPE or PEEK, or any other suitable substance. The bumper elements 267 are wide enough to attach to the paired plates or approximately 15-20 mm. The distance between the adjacent spinous process is typically 2-5 cm and the bumpers are sized to fit between adjacent spinous processes.

The dynamic spinal stabilization device 268, when attached to the pair of plates 290, 292 affixed to the spinous processes 302 will advantageously resist excessive spinal flexion. Loss of the normal lordotic curve by simple distraction between the spinous processes 302 by a bumper or spacer element 267 alone may lead to flat back syndrome, kyphosis, and potentially exacerbation of a pre-existing spondylolisthesis. However the addition of the flexible rod of the present invention will function to counteract these undesirable tendencies. Nonetheless, controlled spinal flexion will be permitted by the dynamic spinal stabilization device.

The invention claimed is:

1. An apparatus for stabilizing a patient's spine, comprising:
   a plurality of bullets with each bullet having an upper side and a lower side wherein the bullet's upper side is sized and configured to insert into an adjacent bullet's lower side in a manner forming a rod wherein a top bullet is on the top of the rod and a bottom bullet is on the bottom of the rod;
   an extension spring that resists elongation wherein said extension spring is disposed around and encases the rod and the extension spring is attached to the rod in a manner to resist separation of the individual bullets wherein, upon elongation of the extension spring, the bullets' upper sides withdraw from the adjacent bullets' lower sides allowing the bullets to move and bend in all planes with respect to the adjacent bullets, and wherein the top bullet is attachable to a part of a patient's spine by an attachment means and the bottom bullet is attachable to a second part of the patient's spine by an attachment means;
   a sleeve of woven material disposed around and encases the extension spring in a manner that provides an elongation limit to the spring wherein the sleeve is in a loose weave pattern when the extension spring is in a resting, non elongated state and upon elongation of the extension spring, the sleeve elongates, tightening the sleeve's woven material resulting in a constricted diameter of the sleeve; and
   a compression spring disposed around and encases the sleeve of woven material and bullets in a manner to resist compression of the bullets with respect to each other.

2. The apparatus for stabilizing a patient's spine of claim 1, wherein each bullet is attached to the adjacent bullet by a flexible attachment material to flexibly attach the bullets together in a manner to provide for terminal elongation of the rod;
   further comprising a top attachment element attached to the top bullet;
   a bottom attachment element attached to the lower bullet.

3. The apparatus for stabilizing a patient's spine of claim 1, wherein, the bullets' upper sides are conically shaped.

4. The apparatus for stabilizing a patient's spine of claim 1, wherein, the bullets have a generally uniform lateral curved shape in a manner that forms a curved rod shape.

5. The apparatus for stabilizing a patient's spine of claim 1, further comprising:
   a guide wire;
   wherein, the bullets have a central passage disposed from the bullet's top side to the bullet's bottom side with the passage sized for insertion of the central guide wire with the central guide wire disposed through the bullets' aligned central passages.

6. The apparatus for stabilizing a patient's spine of claim 1, wherein the attachment means to connect the bullets to the spine comprises a first transverse rod and second transverse rod with each transverse rod having a first end and second end and a midbody wherein the top bullet is attached to the midbody of the first transverse rod and the first end of the first transverse rod is attachable to a part of the patient's spine and the second end of the first transverse rod is attachable to a second part of the patient's spine and the bottom bullet is attached to the midbody of the second transverse rod wherein first end of the second transverse rod is attachable to a third part of the patient's spine and the second end of the second transverse rod is attachable to a fourth part of the patient's spine.

7. The apparatus for stabilizing a patient's spine of claim 6, wherein, at least one of the transverse rods is shaped and attached to one of the bullets in a manner that the distance between the first end of the first rod and the first end of the second rod is less than the length of the interconnected bullets.

8. The apparatus for stabilizing a patient's spine of claim 1, wherein the attachment means that attaches the rod to the spine comprises a first plate and a second plate with each plate having a midbody and the first plate and second plate are attachable a patient's spine.

9. The apparatus for stabilizing a patient's spine of claim 8, further comprising:
   a first bumper attached to the first plate;
   a third plate and a fourth plate;
   a second bumper attached to the third plate;
   wherein the third plate and fourth plate are attachable to an adjacent spinous process;
   wherein the first bumper and second bumper fit snugly adjacent to each other.

10. An apparatus for stabilizing a patient's spine, comprising:
    a plurality of bullets with each bullet having an upper side and a lower side, wherein the bullet's upper side is sized and configured to insert into an adjacent bullet's lower side to form a rod wherein a to bullet is on a top of the rod and a bottom bullet is on a bottom of the rod;

a spring that resists elongation wherein said spring is disposed around and encases the rod and the spring is attached to the rod to resist separation of the individual bullets wherein, upon elongation of the spring, a bullet's upper side withdraws from an adjacent bullet's lower side, allowing each bullet to move and bend with respect to the adjacent bullet;

a sleeve of woven material disposed around and encases the spring to provide an elongation limit to the spring wherein the sleeve is in a loose weave pattern when the spring is in a resting, non elongated state, and upon elongation of the spring, the sleeve elongates, tightening the sleeve's woven material resulting in a constricted diameter of the sleeve; and a compression spring disposed around and encases the sleeve of woven material and bullets in a manner to resist compression of the bullets with respect to each other;

wherein, the to bullet is attachable to a first part of a patient's spine and the bottom bullet is attachable to a second part of the patient's spine; and wherein each bullet is attachable to the adjacent bullet by a flexible material to flexibly attach the bullets together to provide for elongation of the rod.

11. The apparatus for stabilizing a patient's spine of claim 10, further comprising:
a guide wire;
wherein the bullets have a central passage disposed from the bullet's top side to the bullet's bottom side with the passage sized for insertion of the central guide wire disposed through the bullets' aligned central passages.

12. The apparatus for stabilizing a patient's spine of claim 10, further comprising:
an attachment device to connect the bullets to the spine comprises a first transverse rod and second transverse rod with each transverse rod having a first end and second end and a midbody, wherein the top bullet is attached to the midbody of the first transverse rod and the first end of the first transverse rod is attachable to a part of the patient's spine and the second end of the first transverse rod is attachable to a second part of the patient's spine, and the bottom bullet is attached to the midbody of the second transverse rod wherein first end of the second transverse rod is attachable to a third part of the patient's spine and the second end of the second transverse rod is attachable to a fourth part of the patient's spine.

13. The apparatus for stabilizing a patient's spine of claim 12,
wherein at least one of the transverse rods is shaped and attached to one of the bullets such that a distance between the first end of the first rod and the first end of the second rod is less than a length of the interconnected bullets.

14. The apparatus for stabilizing a patient's spine of claim 10, further comprising:
an attachment device for attaching the rod to the spine, including a first plate and a second plate with each plate having a midbody and the first plate and second plate are attachable a patient's spine.

* * * * *